US011475630B2

(12) United States Patent
Tian et al.

(10) Patent No.: US 11,475,630 B2
(45) Date of Patent: Oct. 18, 2022

(54) SYSTEM AND METHOD FOR GENERATING ACUPUNCTURE POINTS ON RECONSTRUCTED 3D HUMAN BODY MODEL FOR PHYSICAL THERAPY

(71) Applicant: MIDEA GROUP CO., LTD., Foshan (CN)

(72) Inventors: Yuan Tian, Sunnyvale, CA (US); Suresh Mani, Fremont, CA (US)

(73) Assignee: MIDEA GROUP CO., LTD., Foshan (CN)

( * ) Notice: Subject to any disclaimer, the term of this patent is extended or adjusted under 35 U.S.C. 154(b) by 529 days.

(21) Appl. No.: 16/560,913

(22) Filed: Sep. 4, 2019

(65) Prior Publication Data

US 2020/0126297 A1   Apr. 23, 2020

Related U.S. Application Data

(63) Continuation-in-part of application No. 16/351,334, filed on Mar. 12, 2019, now Pat. No. 11,197,799.
(Continued)

(51) Int. Cl.
*G06T 17/20* (2006.01)
*G06T 7/70* (2017.01)
(Continued)

(52) U.S. Cl.
CPC ............ *G06T 17/20* (2013.01); *G06T 7/0012* (2013.01); *G06T 7/55* (2017.01); *G06T 7/70* (2017.01);
(Continued)

(58) Field of Classification Search
CPC ... A61B 5/389; A61B 5/1116; A61B 5/14542; A61B 5/4836; A61B 5/7278;
(Continued)

(56) References Cited

U.S. PATENT DOCUMENTS 11,197,799 B2    12/2021  Tian et al.
2017/0189268 A1*   7/2017  Chai .................... A61B 5/4854
(Continued)

FOREIGN PATENT DOCUMENTS

CN    104680582 A    6/2015
CN    106164978 A    11/2016
(Continued)

OTHER PUBLICATIONS

Midea Group Co., Ltd., ISRWO, PCT/CN2019/110898, Dec. 30, 2019, 8 pgs.
(Continued)

*Primary Examiner* — Xilin Guo
(74) *Attorney, Agent, or Firm* — Morgan, Lewis & Bockius LLP

(57) ABSTRACT

System and method for generating acupuncture points on reconstructed 3D human body mesh for physical treatment are disclosed. The computing device obtains a first two-dimensional image of a human subject that captures at least a predefined portion of the human subject; processes the first two-dimensional image of the first human subject using a trained human body recovery model to obtain a plurality of parameters representing a three-dimensional human body mesh with corresponding acupuncture points. The trained human body recovery model includes an iterative three-dimensional regression module that is supervised by a discriminator and that minimizes a combined loss below a preset threshold. The combined loss includes a discriminator error that provides a measure of whether the obtained three-dimensional human body mesh with corresponding acupuncture points correspond to real human shape, pose, and acupuncture points.

20 Claims, 16 Drawing Sheets

Related U.S. Application Data

(60) Provisional application No. 62/747,065, filed on Oct. 17, 2018.

(51) Int. Cl.
| | |
|---|---|
| *G06T 7/00* | (2017.01) |
| *G06T 7/55* | (2017.01) |
| *G06T 19/00* | (2011.01) |
| *A61B 5/00* | (2006.01) |

(52) U.S. Cl.
CPC ............ *G06T 19/00* (2013.01); *A61B 5/0077* (2013.01); *G06T 2207/20081* (2013.01); *G06T 2207/30196* (2013.01); *G06T 2210/41* (2013.01); *G06T 2215/16* (2013.01); *G06T 2219/004* (2013.01)

(58) Field of Classification Search
CPC . A61B 5/0816; A61B 5/4854; A61B 5/02055; A61B 5/0532; A61B 5/0077; A61B 2562/04; A61B 2576/02; G06T 7/70; G06T 7/75; G06T 7/0012; G06T 7/55; G06T 19/00; G06T 17/20; G06T 2215/16; G06T 2219/004; G06T 2210/41; G06T 2207/30004; G06T 2207/20101; G06T 2207/20081; G06T 2207/30196; G06T 19/20; G06T 17/00; G06T 13/40
See application file for complete search history.

(56) References Cited

U.S. PATENT DOCUMENTS

| | | | |
|---|---|---|---|
| 2019/0057521 A1* | 2/2019 | Teixeira | ............... G06N 3/0445 |
| 2019/0343717 A1* | 11/2019 | Yim | ...................... A61B 5/004 |
| 2020/0121556 A1 | 4/2020 | Tian et al. | |
| 2021/0059762 A1* | 3/2021 | Ng | ...................... A61B 5/7425 |

FOREIGN PATENT DOCUMENTS

| | | |
|---|---|---|
| CN | 106952333 A | 7/2017 |
| CN | 107729797 A | 2/2018 |
| WO | WO 2017191878 A1 | 11/2017 |

OTHER PUBLICATIONS

Midea Group Co., Ltd., IPRP, PCT/CN2019/110898, Apr. 14, 2021, 5 pgs.
Midea Group Co., Ltd., 1st U.S. Non-Final Office Action, U.S. Appl. No. 16/351,334, dated Aug. 2, 2021, 7 pgs.

* cited by examiner

300

310
Provide a plurality of 2D annotated images, a pool of 3D meshes of human bodies of varying shapes and poses, and 3D datasets including 3D data of acupuncture points marked on respective 3D meshes of human bodies

↓

320
Obtain a single 2D image of at least a portion of a human subject and convolutional features of the 2D image

↓

330
Process the 2D image using a trained human body recovery model to reconstruct a 3D human body mesh of the human subject with acupuncture points based on a plurality of parameters that are related to shape, pose, acupuncture points of the human subject, and camera parameters (e.g., global rotation, translation, scale) for taking the 2D image, for example, including reshaping a 3D body mesh using the shape and pose parameters, and projecting (e.g., orthographic projection) key physical points and acupuncture points onto the reconstructed 3D human body mesh

↓

340
Perform iterative 3D regression to output a 3D human body mesh with a minimized combined loss including (1) a joint reprojection error related to projection errors of a plurality of key physical points collectively, (2) a 3D ground truth error related to 3D joint losses, 3D shape and pose losses, and 3D acupuncture point losses, and (3) a discriminator error

↓

350
Output a reconstructed 3D human body mesh for the human subject, the 3D human body mesh marked with acupuncture points

↓

360
Generate treatment data associated with respective acupuncture points for the human subject in accordance with the reconstructed 3D human body mesh with acupuncture points corresponding to the human subject

Figure 3

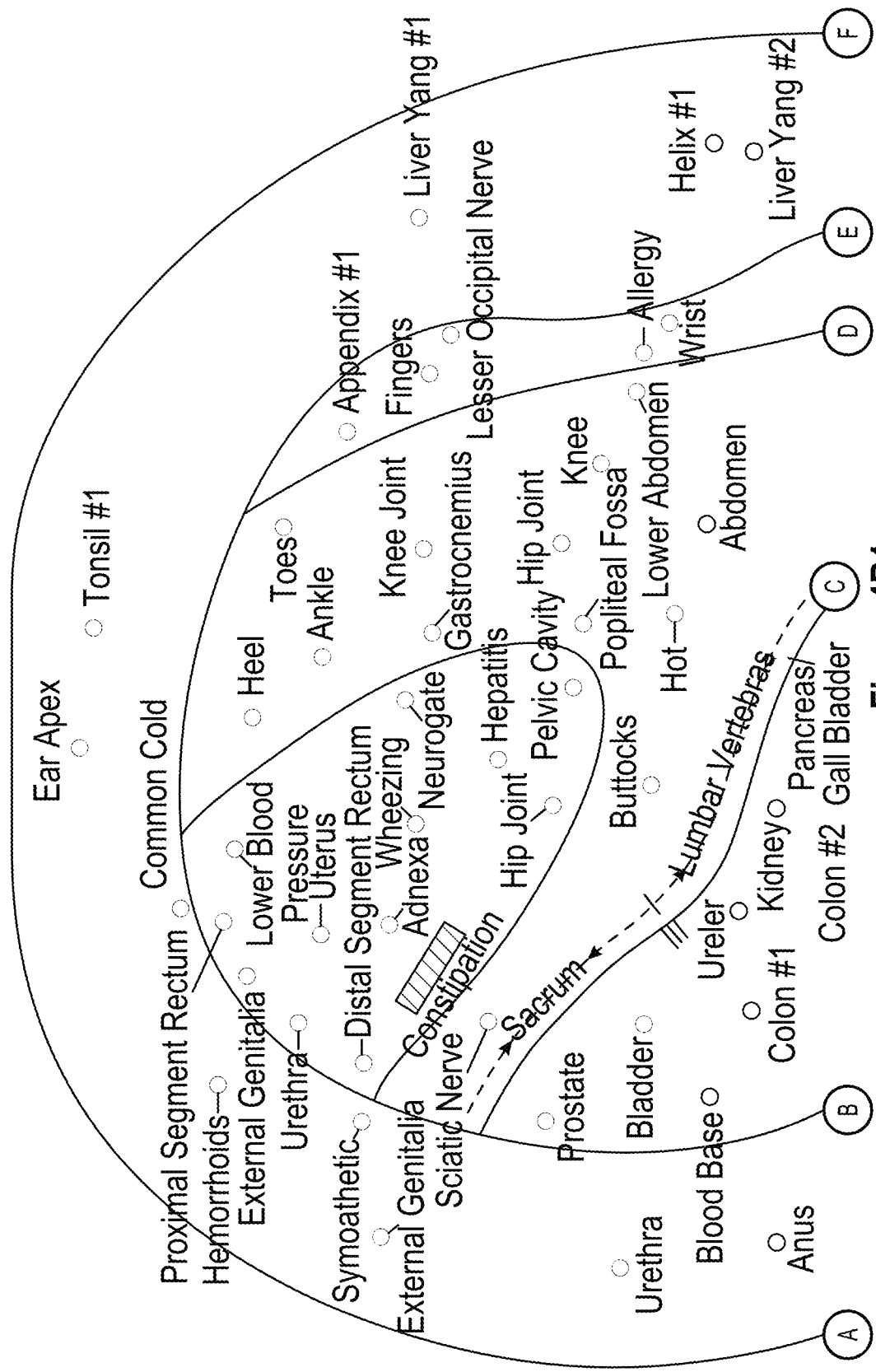
Figure 4B1

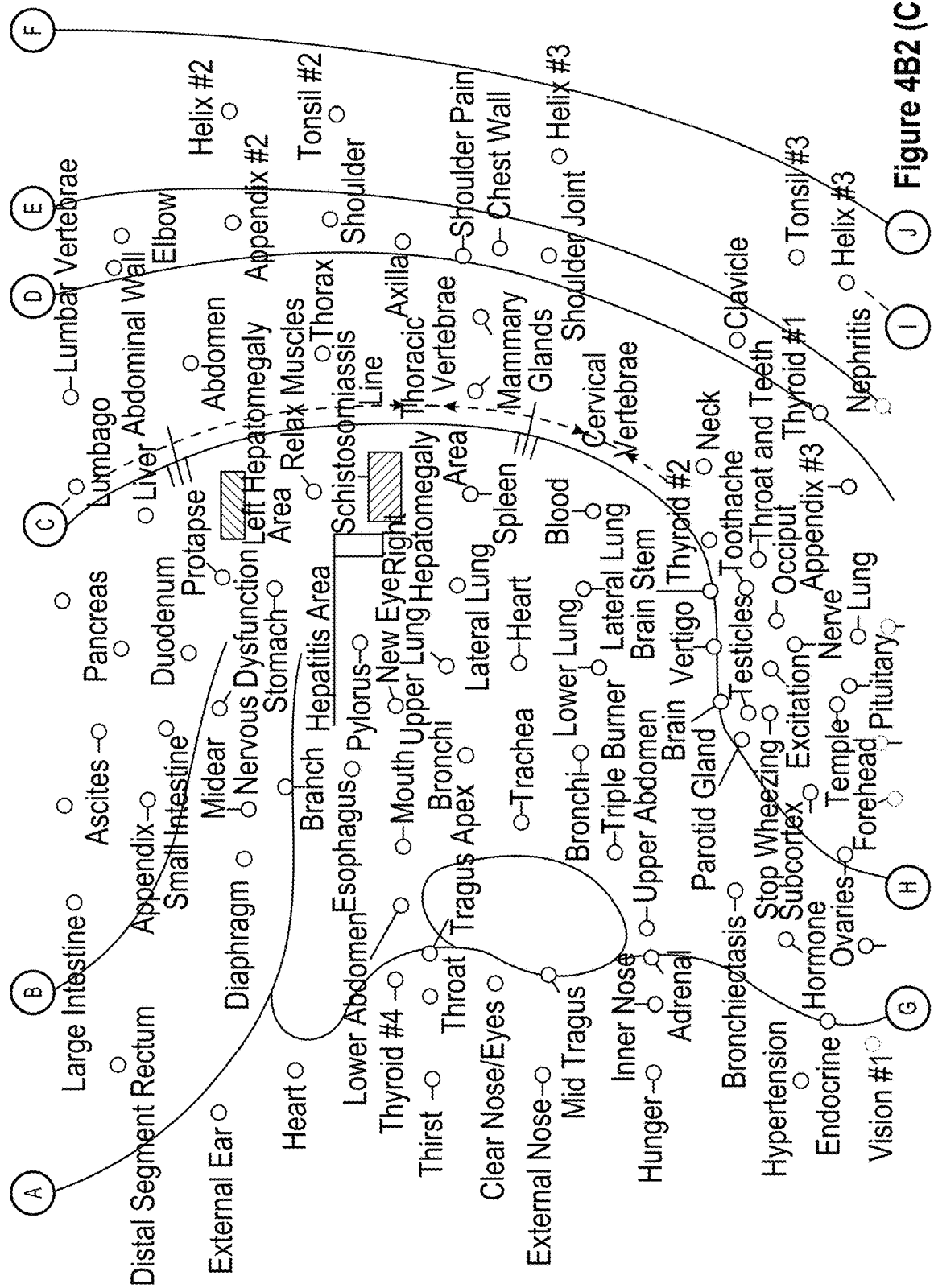
Figure 4B2 (Continued)

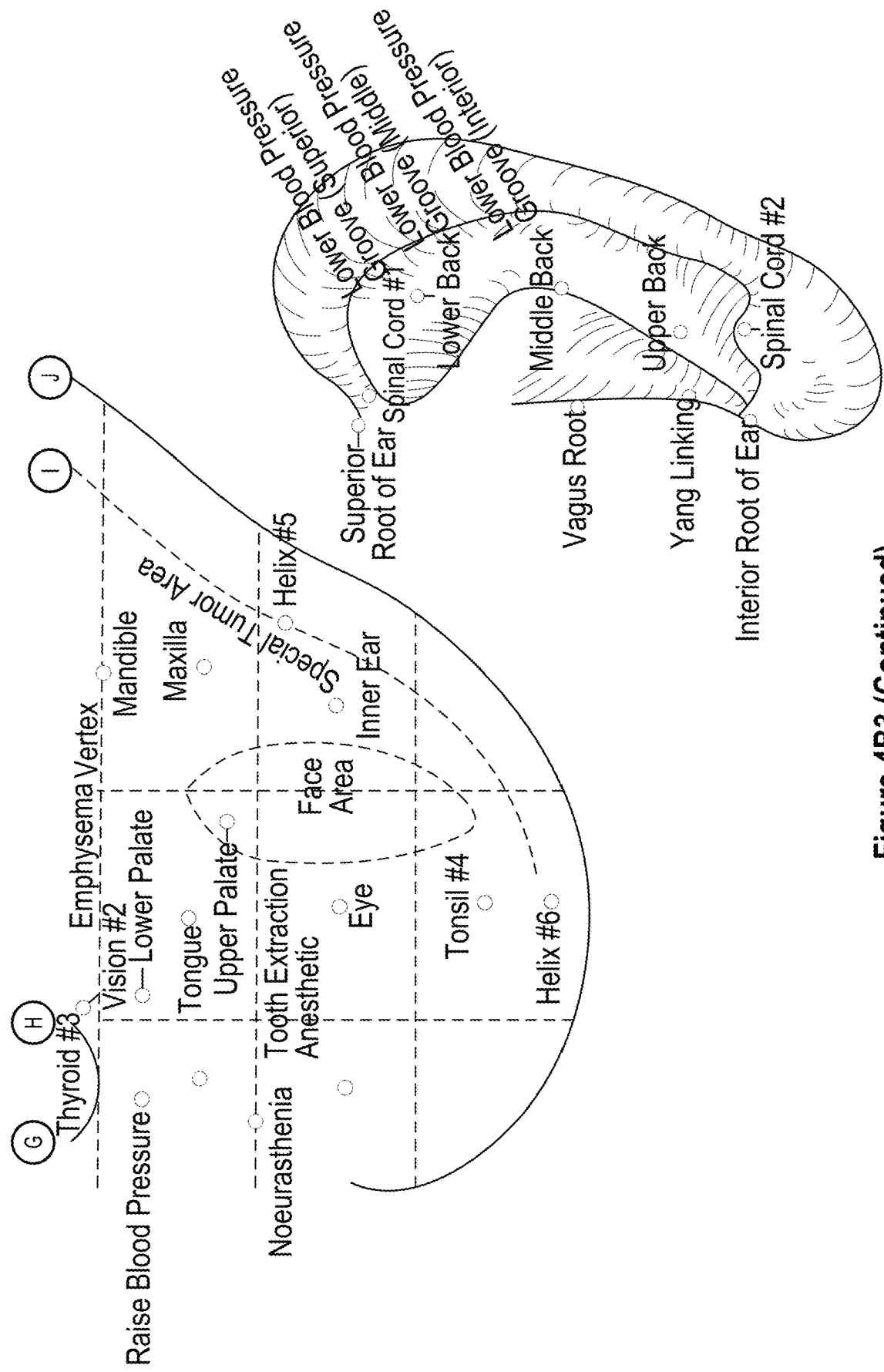
Figure 4B3 (Continued)

SYSTEM AND METHOD FOR GENERATING ACUPUNCTURE POINTS ON RECONSTRUCTED 3D HUMAN BODY MODEL FOR PHYSICAL THERAPY

RELATED APPLICATION

This application claims the benefit of U.S. Provisional Patent Application No. 62/747,065, filed Oct. 17, 2018, and is a continuation-in-part of U.S. patent application Ser. No. 16/351,334, filed Mar. 12, 2019, all of which are incorporated herein in their entireties.

TECHNICAL FIELD

This relates generally to therapeutic technologies, including but not limited to detecting pressure points for acupuncture and therapeutic physical manipulations to human patients.

BACKGROUND

Recently physical therapy that involves acupuncture treatments, pressure point therapy, deep tissue massages, targeted heat treatments, targeted ice treatment, target electric muscle stimulation therapies, etc. are widely adopted and used. A common element in these different types of treatments is that they all involve targeted actions (e.g., insertion of acupuncture needles, application of electric pulses, application of heating, ice pack, and/or pressure, etc.) performed in accordance with specific locations on a patient's body (e.g., pressure points, acupuncture points (Xue Wei), trigger points, knots, cramp/spasm sites, joints, etc.) that are identified by treatment personnel. A patient typically gets evaluated in person by a physical therapist, massage therapist, a traditional oriental medicine doctor, a personal trainer, or some other experts that are skilled at identifying the problems that the patient has with his/her muscles, joints, body, health and/or wellbeing, determining suitable treatment procedures, and determining suitable locations on the body that should be treated with the identified treatment procedures. The therapy itself requires the treatment personnel to physically perform the procedures on the patient's body, to help the patient achieve relaxation, pain reduction, reduction of physical symptoms, improving circulation, healing of injuries, and ultimately improved health and/or wellbeing for the patient.

There are multiple issues with the above treatment practices. First, it requires many years of studying and practicing to achieve the skill level of a trained practitioner in the field of physical medicine. The lack of qualified teachers and institutions overall in this field make it difficult to spread the knowledge and expertise in this very rich and diverse field. In addition, the practices require not only mental acuity and talent, but also physical skills that take much practice to develop. Many patients do not want to become the subject of a novice practitioner, and as a result, it takes much longer for a novice to become a skilled practitioner. A lot of the treatment procedures performed by the practitioners require not only knowledge and skill, but also physical strength and stamina. A lot of skilled and experienced practitioner cannot continue to practice effectively because they are advanced in years and are easily fatigued due to the physical demand of the practice.

Other aspects of physical therapy may prevent it from becoming as widely utilized includes privacy concerns, hygienic concerns, and time/space limitations. For example, some patients are reluctant to try out treatments involving physical manipulations because they are uncomfortable with the extent of physical contact and/or close physical proximity of the therapist, or remaining undressed for an extended period of time during the treatment process. Some people are uncomfortable with going to a facility where massage tables and equipment have been shared with other patients. Sometimes, a well-regarded treatment facility may be overbooked, or have unreasonably long wait-times.

Although there have been some attempts at addressing some of the issues outlined above. The solutions are far from adequate. For example, automatic massage chairs can be used to perform massages in accordance with a few preset programs targeting various locations of the body (e.g., back, legs, shoulders, etc.) or having predefined goals (e.g., relaxing muscles, reducing back pain, improving circulation, etc.). However, the massage chair and the preset programs are not tailored to individual patients, and do not work well for many patients (e.g., due to variations in size, height, symptoms, injuries, etc.). Handheld massage devices or electric muscle stimulation devices allow patients to self-direct the device to the locations on his/her bodies that need treatment. However, due to the lack of skills and diminished physical capabilities due to age, pain, and injuries on the part of the patients, the effectiveness of the self-help devices are low as well. Videos and self-help books on self-administered and armature-administered treatment may help in some low-risk scenarios, but pose increased problems and harm to the patients for more complex treatment scenarios. Although one may contemplate remotely controlling a massage device to treat a patient, real research and development on this front is very limited to date.

It is challenging to provide an effective and efficient human-machine interface that facilitates remotely-guided acupuncture and therapeutic physical manipulations. Good techniques for supporting expert guidance, and indirect and/or intermittent expert intervention during remotely-guided physical therapeutic treatment of a patient (e.g., by a local operator, or a robot) in real-time over a network are in great need.

SUMMARY

Accordingly, there is a great need for an effective and efficient human-machine interface that facilitates remotely-guided acupuncture and therapeutic physical manipulations, and for good techniques for supporting expert guidance, and indirect and/or intermittent expert intervention during remotely-guided physical therapeutic treatment of a patient (e.g., by a local operator, or a robot).

In this disclosure, a treatment environment includes a local site (e.g., local site 102 as shown in FIG. 1A) and a remote site (e.g., remote site 105 as shown in FIG. 1B). A patient is located at the local site with a therapeutic robot and/or a local human treatment operator. Two-dimensional (2D) images of the patient (e.g., images of the patient's full body or one or more parts/segments of the patient's body) streamed from the local site are provided to a computing system (e.g., the local computing device 114 in FIG. 1A, or the remote computing device 115 or the central control server 136 in FIG. 1B) which processes the captured 2D images and generates three-dimensional (3D) human body mesh marked with acupuncture points and other corresponding key physical points (e.g., joints, muscles, trigger points, pressure points, etc.) for the patient's body. In some embodiments, the 2D images and corresponding locations for the acupuncture points are continuously updated and tracked in real-time during a treatment session, such that the treatment can be administered to the correct locations on the patient's body throughout the treatment session, even when the patient has moved its body and/or changed his/her posture (e.g., due to application of force, sensitivity or discomfort caused by the treatment, and/or fatigue caused by a fixed posture, etc.).

In some embodiments, the computing system includes a human body recovery model that is trained to reconstruct a 3D human body mesh in accordance with shape, pose, acupuncture points, and camera parameters that are encoded from the image features extracted from a single 2D image of the patient captured at the local site. In some embodiments, the human body recovery model includes a iterative 3D regression module that minimizes a combined loss. In some embodiments, the combined loss includes a discriminator error that is supervised by a discriminator network/module (e.g., including a plurality of discriminators corresponding to respective acupuncture points, shape, pose, etc.) for evaluating whether the obtained 3D human body mesh marked with acupuncture points correspond to real human shape, pose, and acupuncture points so as to optimize the performance of the human body recovery model. In some embodiments, the combined loss further includes reprojection losses (or errors) and 3D ground truth losses when 2D annotation data (or 2D ground truth data) and/or 3D annotation data (or 3D ground truth data) are available. In some embodiments, the 2D images are annotated with 2D keypoints based on database such as LSP, MPII, MPI-INF-3DHP, or COCO.

In some embodiments, a patient or a local treatment operator can perform the treatment to the identified location(s) in accordance with the treatment data associated with the marked acupuncture points on the 3D human body mesh provided based on the locally captured images. This allows less skilled personnel or the patient himself to administer the treatment, reducing the demand on highly skilled practitioners to be physically present at the patient's site to administer the treatment. The system and process discussed in the current disclosure can also be used for training junior practitioners by supervising and guiding their skills in identifying acupuncture points on patients with different height and weight and in different poses. This is also more effective than administering the treatment based on online demo videos or text books, because the acupuncture points are identified for the patient's particular body and posture, and are updated in real-time to maintain accuracy of the locations. For certain areas of the body or certain types of lower risk treatment, the patient or his/her caregiver can perform the treatment at the patient's home with better privacy and convenience to the patient.

In some embodiments, in addition to the local site, the treatment environment includes a remote site, where a mixed reality environment is utilized for a remote expert to perceive the 3D human body mesh corresponding to the patient's body (e.g., through point cloud images or other 3D rendering of the patient's body, and haptic feedback provided on a haptic input device) and provide treatment guidance inputs (e.g., verbal instructions, haptic movement demonstration instructions, etc.) as needed. At the remote site, the patient's 3D human body is displayed and marked with the acupuncture points and the key physical points that have been identified by the computing system. In some embodiments, the remote expert (e.g., Traditional Chinese Medicine doctors) can provide ground truth data (e.g., annotation data) of the acupuncture points on 2D images and/or 3D human body models/mesh of various shapes and/or poses. In some embodiments, the remote expert can also adjust the locations of the marked acupuncture points based on his own personal expertise, and/or select a subset of them for particular treatment procedures. The remote expert can provide high-level instructions to the patient and/or the local treatment operator to execute the treatment procedures to one or more regions of the patient's body in sequence. In accordance with this remote expert-facilitated mixed-reality setup, the remote expert can help monitor and guide the treatment of multiple patients respectively located at multiple different locations at the same time. The remote expert can be relieved from the physically demanding and strenuous tasks of manually administering the treatment, such that his/her experience, knowledge, and expertise can be utilized over a longer period of time within each day, and in the long term. In some embodiments, the 3D human body mesh marked with acupuncture points corresponding to the patient's body can be presented in lieu of a full-color photographic images or video of the patient to the remote expert, such that the patient's discomfort and concern related to body image and privacy can be addressed and relieved.

In some embodiments, various sensors are provided at the local site to collect sensor information during treatment. The sensor information is processed in conjunction with the treatment being administered and the result of the analysis is provided to the local operator and/or remote expert in real-time such that suitable adjustment may be made. For example, the remote expert may be presented with the changes in the user's posture, regional temperatures of various parts of the patient's body, stiffness of various parts of the patient's body, heart rate, blood pressure, respiratory rate, perspiration, etc., and adjust the treatment procedures and/or treatment locations on the patient's body accordingly. The additional sensor feedback and analysis results help the remote expert to perform better guidance during treatment and adjust treatment in real-time in accordance with the patient's conditions and tolerance to the treatment.

In some embodiments, in addition to a local treatment operator, a therapeutic robot (e.g., robot arms, message pads on chair or bed, movable pressure applicators, etc.) located at the local site is utilized and controlled to administer at least some of the physical treatments applied to the patient's body. For example, acupuncture needle insertion and removal, heat application via infrared light or direct contact, ice pack application, pressure application via applicators of various shapes and sizes, application of rolling and massage motions in accordance with a movement path, controlled stretching of a part of the body, etc. can be performed by the therapeutic robot in accordance with the instructions received from the computing system, the patient, the local treatment operator, and/or the remote expert. The robot's motion is more precise, consistent, and fully adjustable, and can continuously function for extended period of time without fatigue like a human operator or practitioner would be. The robot is easy to sanitize and also gives the patient more privacy.

In one aspect, a method is performed at a computing device having one or more processors and memory, the method includes: obtaining a first two-dimensional image of a human subject, the first two-dimensional image of the first human subject captures at least a predefined portion of the first human subject; processing the first two-dimensional image of the first human subject using a trained human body recovery model to obtain a plurality of parameters representing a three-dimensional human body mesh with corresponding acupuncture points, wherein: the trained human body recovery model includes an iterative three-dimensional regression module that is supervised by a discriminator and that minimizes a combined loss below a preset threshold, the combined loss including a reprojection error of an encoded two-dimensional input image of a human body, a three-dimensional ground truth error, and a discriminator error; the three-dimensional ground truth error includes respective errors related to a pose estimation, a shape estimation, and an acupuncture points estimation relative to annotated three-dimensional human bodies; and the discriminator error provides a measure of whether the obtained three-dimensional human body mesh with corresponding acupuncture points correspond to real human shape, pose, and acupuncture points. The method further includes generating treatment data corresponding to the first human subject in accordance with the obtained three-dimensional human body mesh with corresponding acupuncture points.

In accordance with some implementations, a computing system includes one or more processors, memory, and one or more programs; the one or more programs are stored in the memory and configured to be executed by the one or more processors and the one or more programs include instructions for performing the operations of any of the methods described above. In accordance with some implementations, a non-transitory computer readable storage medium has stored therein instructions which when executed by a computing system with one or more processors, cause the computing system to perform the operations of any of the methods described above. In accordance with some implementations, a computing system includes means for performing the operations of any of the methods described above.

Additional advantages of the disclosed systems and methods are described throughout this disclosure, and/or are apparent to a person skilled in the art in light of the disclosure provided herein.

BRIEF DESCRIPTION OF THE DRAWINGS

For a better understanding of the various described implementations, reference should be made to the Description of Implementations below, in conjunction with the following drawings in which like reference numerals refer to corresponding parts throughout the figures.

FIG. 3 illustrates an exemplary processing pipeline for training and using a model for generating acupuncture points and providing corresponding treatment data on a reconstructed 3D human body, in accordance with some embodiments.

FIGS. 4(A)-4(E) illustrate exemplary 3D full-body map and acupuncture points maps, respectively (e.g., a full-body map in FIG. 4(A) and acupuncture points maps in FIGS. 4(B)-(E)) of various portions of a human body, in accordance with some implementations.

Like reference numerals refer to corresponding parts throughout the several views of the drawings.

DESCRIPTION OF IMPLEMENTATIONS

Figure 1A:
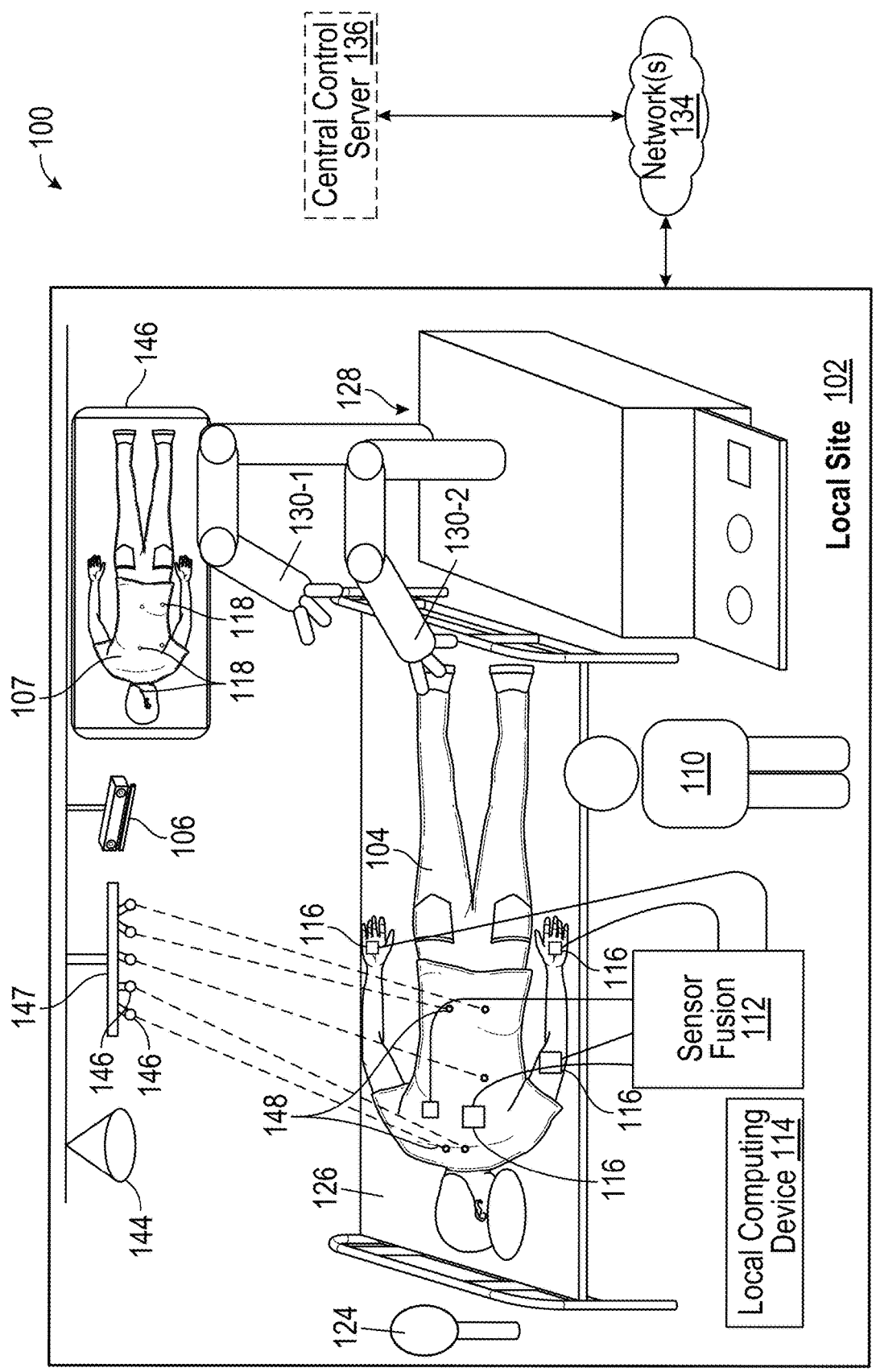
FIG. 1A is an exemplary local site of an exemplary treatment environment that provides remotely-guided acupuncture and therapeutic physical manipulations to a patient, in accordance with some embodiments.

This disclosure provides system and method for reconstructing a 3D human body mesh marked with acupuncture points based on a single 2D image of the patient using a trained human body recovery model including a iterative 3D regression module in accordance with various embodiments.

Remotely-guided acupuncture and therapeutic physical manipulations have advantages over in-person treatment by skilled practitioners due to its flexibility and reduced demand on the skill-levels, physical presence, and/or physical strength and stamina of the treatment operators. A single skilled practitioner can provide remote assistance and guidance to a great number of local sites staffed with less skilled human treatment operators, remotely guided therapeutic robots, or just the patients themselves. This way, a greater number of patients can be treated, without the patients having to travel long distances or accommodating inconvenient treatment schedules. At the same time, the expertise of the remote expert can be utilized for complex diagnosis and treatment plan designs, with the aid of computer-generated key physical points that are fitted to the individual patients' particular body parameters. The accuracy of the diagnosis and treatment plan generation can be improved because of the combination of expert input and vast knowledge base of the computing system that generates the acupuncture points on the 3D reconstructed human body mesh for the patient's body.

With the availability of remotely-guided treatment plans and real-time adjustment and guidance input from the remote expert, patients who are traditionally reluctant to go to such direct contact physical manipulation therapies can benefit from these types of treatments. For example, some patients do not want to undress in front of a real human practitioner or be directly touched by a human practitioner for various reasons (e.g., body image, modesty, religion, hygiene, etc.). The remote guidance system disclosed herein allows the patient to be alone in a treatment room or his/her own home, and have the treatment procedure performed by a robot or by himself/herself, with the guidance provided by a trained computer system and a skilled expert in real-time based on real-time images of his/her body and posture. The skilled expert does not need to see a color image of the patient or know the patient's identity, when providing the remote guidance input based on a 3D human body mesh of the patient's body (e.g., a mono-color depth image) and corresponding acupuncture points generated by the computing device. The skilled expert can explore the surface haptic characteristics of the 3D human body mesh and receive haptic feedback generated based on physics simulation via a haptic-enabled input device. The skilled expert also receives real-time sensor information collected from the patient's body and patient's verbal feedback during treatment. These further helps to reduce the limitations of a remote consultation, and improves the accuracy of the remote guidance provided by the skilled expert.

With the use of a therapeutic robot at the local site, the physical demand on the treatment staff is reduced. Instead of using fixed programs and instructions that are generic to many patients, the therapeutic robot can deliver customized treatment based on preprogrammed instructions with intermittent aid of a remotely located human expert. On the one hand, the robot is programmed to perform various low level or intermediate level tasks in accordance with environment input collected via on-board sensors and/or through a network. On the other hand, a human expert can intervene indirectly at suitable times in accordance with actual real-time visual and haptic rendering of the patient's 3D human body mesh with the acupuncture points using a trained and supervised human body recovery model. In some embodiments, the generation of acupuncture points is based on the human body recovery model that is supervised using a 3D iterative regression model including a discriminator module with ground truth annotation data (e.g., 2D and/or 3D data of acupuncture points, pose, shape, and/or other key physical points) of many patients with varied physical characteristics and therapeutic needs. As a result, the locations of the key physical points presented to the remote expert for treatment plan generation and used by the robot for performing the treatment procedures that are highly customized and accurate for the individual patients. Further, using the trained human body recovery model, only a single 2D image of the patient including either full body or a portion of the body is needed for reconstructing a 3D human body mesh marked with acupuncture points, thus providing the end-to-end solution to the need of the physical therapy.

Individual features or combinations of features of the remotely-guided physical treatment system as described herein in various embodiments will further the advantages set forth above and/or provide additional advantages which will be elaborated on in more detail or will be apparent to a person skilled in the art in light the present disclosure.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skills in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first user interface could be termed a second user interface, and, similarly, a second user interface could be termed a first user interface, without departing from the scope of the various described implementations. The first user interface and the second user interface are both user interfaces, but they are not the same user interface.

The terminology used in the description of the various described implementations herein is for the purpose of describing particular implementations only and is not intended to be limiting. As used in the description of the various described implementations and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

It is to be appreciated that "remotely guided" may refer to control over a wired or wireless network, such as the Internet, or an intranet within an organization or household network, the exact distance or location from which the inputs from the human user is provided is not specifically limited, and the scope of the present teachings is not so limited, unless explicitly specified otherwise.

It is also to be appreciated that while the terms user, expert, human operator, administrator, technician, person, and the like may be used to refer to the person or persons acting in the context of some particularly situations described herein, these references do not limit the scope of the present teachings with respect to the person or persons who are performing such actions.

FIG. 1A is an exemplary local site 102 of a remotely guided physical treatment environment 100 in accordance with some embodiments. At the local site 102 of the environment 100, a patient 104 is collocated with a number of sensors, including imaging sensors (e.g., camera 106), physiological sensors 116 (e.g., blood pressure monitor, heart rate monitor, oxygen level monitor, EMG (Electromyography) sensors, temperature sensors, perspiration sensors, etc.), patient feedback sensors (e.g., pressure sensors, microphones 124). The patient 104 is positioned on a support surface 126, such as the top of a massage table, a motorized bed, or a treatment chair. All the sensors are optionally connected to a network 134 and configured to transmit collected sensor data to a central control server 136 (e.g., a central computing system) in real-time and be controlled by the central server in real-time over the network 134. In some embodiments, the sensors are optionally controlled manually (e.g., adjusting the camera view and zoom level) by a local operator 110 via an input interface of the sensors.

In some embodiments, the imaging sensors 106 are configured to capture visual data of the local site. In some embodiments, the imaging sensors 106 are further configured to capture a heat map of the patient's body to indicate the body's reaction to the treatment or indicate blood circulation state and sites of injury of the patient. In some embodiments, the imaging sensors 106 are located above the patient's body while the patient is lying or sitting on the support surface 126. In some embodiments, the imaging sensors 106 capture 2D images while the patient is in a standing posture to generate a 3D full body mesh or a 3D partial human body mesh of the patient using the 3D body recovery model. In some embodiments, the imaging sensors 106 are controlled by the central server 136 to adjust a camera angle and/or zoom level based on the treat location and treatment procedure currently being used. For example, the imaging sensors 106 can be controlled to capture a full body image or a portion of the full body in accordance with the treatment need.

In some embodiments, the physiological sensors 116 (e.g., blood pressure monitor, heart rate monitor, oxygen level monitor, EMG (Electromyography) sensors, temperature sensors, perspiration sensors, etc.) are used to collect baseline patient physiological data, and physiological response data during the treatment or particular sub-portions of the treatment procedures. The response data from different sensors are correlated by time through a sensor fusion process (e.g., in sensor fusion module 112 of the local computing device 114), and provided to an analysis model on the central control server 136 over the network 134. The analysis results, such as increased/reduced muscle/mental stress level, increased/decreased comfort level, increased/decreased mobility/flexibility level, increased/decreased pain, increased/decreased circulation, and other treatment advocacy levels etc., causes the analysis model to generate a recommendation regarding changes in the currently administered treatment procedure or plan.

At the local site 102 of the environment 100, a therapeutic robot 128 (e.g., a robot including robot arms 130-1 and 130-2 and control unit 132) is collocated with the patient 104. The robot 128 is connected to a network 134 and receives instructions from the central control server 136 over the network 134. In some embodiments, the central control server 136 is collocated with the robot 128 (e.g., in the same room). In some embodiments, the central control server 136 is within the same local area network as the robot (e.g., in the same treatment facility). In some embodiments, the central control server 136 is connected to the robot 128 over a wide area network (e.g., the Internet). In some embodiments, multiple robots located at multiple locations are connected and controlled by the same central control server 136 at the same time.

In some embodiments, the robot 128 has multiple attachments (e.g., acupuncture needle ejector, massage roller, acupressure probe, heat pad, ice pad, electrodes, clamps, grabber, etc.) that can be used (e.g., the robot can automatically select the selected attachments based on instructions from a human operator (e.g., local operator 110 or a remote expert 108 located at the remote site 105 (e.g., FIG. 1B))) for different types of treatment procedures (e.g., acupuncture, massage, acupressure, heat, ice, electric muscle stimulation, pressure, stretching, etc.) and/or treatment locations (e.g., pressure points on the head, neck, shoulders, and other parts of the body, joints, muscles, skin, etc.) on the patient's body. In some embodiments, the sensors (e.g., sensors 106, 116, 124, etc.) are optionally controlled manually (e.g., adjusting the camera view and zoom level) by a local operator (e.g., operator 110) via an input interface of the sensors.

In some embodiments, at least some of the physiological sensors and patient feedback sensors are located on the robot 128 and moves with the robot (e.g., with the robot arms 130) to various locations of the patient's body during a treatment procedure. For example, one or more pressure sensors, perspiration sensors, temperature sensors are located on the robot finger tips used during massage and physical manipulations, to detect sites of cramped muscles, sites of inflammation or injury, sites of discomfort or pain, etc., and physiological changes (e.g., increased circulation, relaxation, stiffness, etc.) to the treated sites during various treatment procedures. In some embodiments, at least some of the physiological sensors and patient feedback sensors are attached to fixed locations on the patient's body. For example, a pressure sensor is placed in the patient's hand, and the patient can squeeze it if the treatment (e.g., acupressure, massage, stretching, heat, electric stimulation) is applied with too much force or strength. Other examples include blood pressure monitor, heart rate monitor, and EMG monitors that are attached to fixed locations on the patient's body and transmits sensor data to the local computing device 114 and sensor fusion module 112 in real-time.

In some embodiments, multiple parts (e.g., two robot hands or arms 130 with different primary roles and/or attachments) of the robot 128 can work in a coordinated manner in accordance with the high-level instructions provided by the central control server 136, the remote expert 108, and/or the local operator 110. For example, the robot 128 has onboard processing capabilities to perform low level functions such as moving, pulling, pushing, vibrating, grabbing, moving in a particular selected pattern, and stopping when there is more than a threshold amount of resistance, etc. In some embodiments, the robot 128 has onboard processing capabilities to perform intermediate level tasks, such as grabbing and stretching a limb in a preset direction, applying heat to a treatment site, injecting a needle, removing a needle, applying shiatsu massage to a treatment site, applying percussion massage to a treatment site, applying electric stimulation treatment to a treatment site, wipe a treatment site on the patient's body, applying ointment on a treatment site on the patient's body, helping the patient to lie down or sit up, helping the patient to turn to a required treatment posture, etc. The robot 128 is controlled by the central control server 136 which provides a treatment plan in terms of the low level or intermediate level tasks that can be performed by the robot, where the treatment plan is for accomplishing a high-level instruction provided by the remote expert or the treatment selection program of the central server 136.

In some embodiments, the user feedback sensors include a microphone 124 which captures the sounds of a user (e.g., the patient 104) during treatment. The user may verbally communicate pain or discomfort during treatment, answer the remote expert's questions, or ask questions to the remote expert 108, via the microphone 124. In some embodiments, the patient's speech input (e.g., answers, questions, and comments) during various portions of the treatment session (e.g., intake, diagnosis, treatment, and feedback portions) are analyzed and transcribed by the local computing device 114 automatically into text for record keeping and future improvement of the system.

In some embodiments, the local site 102 includes a number of output devices that provide feedback and information to the patient 104 and the local operator 110. In some embodiments, the local output devices include a display generation component 146, such as a display or a projector, that is used to display a three-dimensional model of the user's body as seen by the remote expert, and current treatment information, such as acupuncture points 118 identified on the patient's body, a current portion of the body that is being manipulated in treatment, and name and explanation of the treatment procedure. In some embodiments, the display also includes an image of the remote expert 108. In some embodiments, the patient's 3D human body mesh, the acupuncture points, and other treatment information are updated in real-time, as the patient shifts his body or change his posture, as the imaging sensors 106 change camera angles and/or zoom to capture 2D images of different portions of the patient's body, as the remote expert modifies the locations of the automatically identified acupuncture points or identifies a subset of the acupuncture points as targeted points for treatment, as the remote expert identifies or changes treatment procedures, and/or as a treatment procedure is performed or completed, etc.

In some embodiments, the output devices include a speaker 144 for outputting verbal questions, answers, and instructions from the remote expert 108 to the patient 104 and/or the local operator 110 during the treatment session.

In some embodiments, the local site 102 includes a projector 147 for projecting the identified acupuncture points (or a subset thereof that are relevant to the current treatment procedure) to their corresponding locations onto the reconstructed patient's 3D body mesh. In some embodiments, the projector 147 is mounted overhead above the patient 104. In some embodiments, the projector 147 is attached to a movable robot arm and can be moved close to a portion of the patient's body that is the subject of the current treatment session (e.g., when the actual treatment is carried out by the patient himself or by the local operator, instead of the robot). In some embodiments, the projector includes multiple light sources 146 that are each individually controlled by the remote server 136 to project a respective light spot 148 onto a respective portion of the patient's body. The precise direction of each light source is calculated based on the coordinates of the spot in three-dimensional space in accordance with the position of the patient's body and the location of a respective acupuncture points on the patient's body. In some embodiments, the images captured with the light spots projected on the patient's body are provided back to the central control server 136 and used to adjust the three-dimensional model of the patient's body, until the actual locations of the light spots projected on the patient's body are aligned with the calculated locations of the light spots on the patient's body at that time.

In some embodiments, the robot arms 130 include sensors that detect and track the locations of the light spots 148 projected onto the patient's body during a treatment procedure, such that the treatment are applied to the correct positions on the patient's body at all times even when the patients moves or changes his/her postures slightly during the treatment. In some embodiments, the projector 147 has a sensor that detects the locations of the robot arms 130 and adjusts its own location and orientations such that the light from the light sources 146 is not blocked by the robot arms 130 on its way to the patient's body.

In some embodiments, at the local site 102, the support surface 126 includes various sensors for collecting physiological feedback and patient feedback. In some embodiments, the support surface 126 also includes various movable components for performing at least part of the treatment procedures. For example, the support surface 126 is the surface of a massage table, and includes balls or round-tipped cylinders that can be moved upward individually against the patient's body to apply various levels of pressure to selected points on the patient's body. The support surface 126 optionally includes massage rollers that travel on the support surface 126 to exert massages on the patient's body with a selected movement pattern. For example, the patient may lie on his back and have his lower back massaged by the rollers with circular motions and up and down motions, once the remote expert has specified or approved the automatically generated motion path for the massage that is tailored for the patient's body. Allowing the patient to lie on his back when receiving the massage is sometimes more comfortable and relaxing for the patient. Because the massage is executed by the massage table according to the reconstructed 3D human body mesh of the patient's body marked with acupuncture points, there is no need for the patient to lie facing down because there is no need for the therapist to see and manipulate the patient's back from above. The moving components of the massage table receives instructions from the central control server 136, and adjusts its movement path of the moving components in real-time during the physical therapy.

In some embodiments, a human treatment operator 110 (e.g., an assistant doctor, a trainee (e.g., a medical student) practicing skills, a nurse, a caregiver, a family member, or a friend of the patient, etc.) is present at the local site 102. The treatment operator 110 can help to perform the treatment in accordance with information and the instructions (e.g., output via the speaker 144 or display generation component 146) provided by the remote expert or the central control server 136. In some embodiments, the treatment operator 110 helps to reposition the patient 104 or keep the patient 104 still during the initial imaging stage (e.g., capturing the 2D image), or to help changing the attachments of the robot 128 for particular treatment procedures that are selected by the remote expert 108. In some embodiments, the human operator 110 can follow the demonstration of the remote expert 108 and perform the corresponding treatment procedure on the patient 104 based on the positions of the light spots 148 projected onto the patient's body.

Figure 1B:
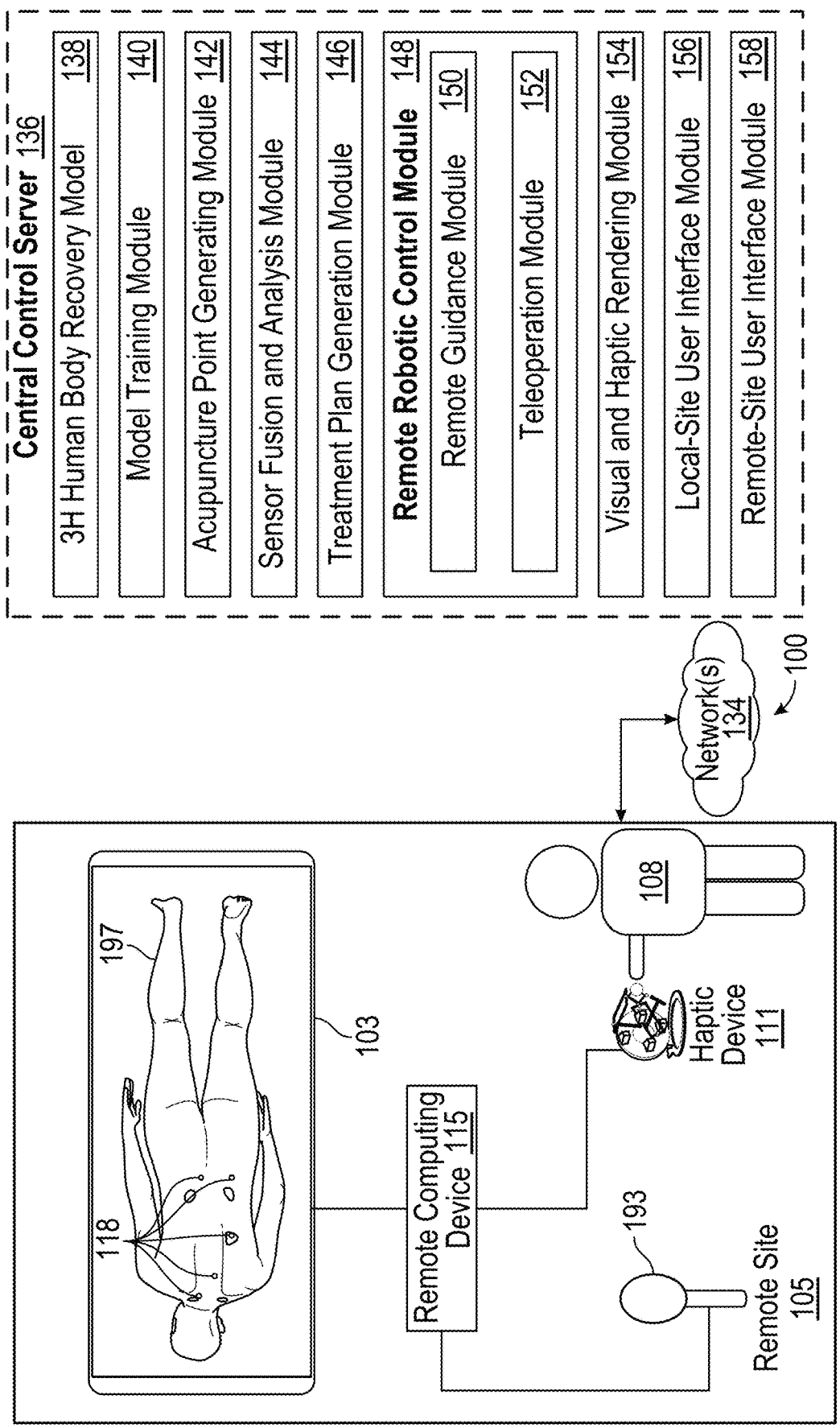
FIG. 1B is an exemplary remote site of the exemplary treatment environment that provides remotely-guided acupuncture and therapeutic physical manipulations to a patient, in accordance with some embodiments.

FIG. 1B is an exemplary remote site 105 of the exemplary treatment environment 100 that provides remotely-guided acupuncture and therapeutic physical manipulations to a patient (e.g., patient 104 in FIG. 1A), in accordance with some embodiment. At the remote site 105 of the environment 100, a display generation component 103, such as a display, a projector, a heads up display or the like, is used to display the reconstructed 3D human body mesh with acupuncture points of the patient 104 based on a 2D image 107 (e.g., FIG. 1A) captured by the imaging sensors 106 located at the local site 102.

In some embodiments, the 2D image of the patient 107 is received from the control server 136, where the control server 136 processes the 2D image to extract image features and continuously update the 2D image of the patient captured by the imaging sensors 106. The control server 136 further reconstructs the 3D human body model 197 (e.g., 3D human body mesh). In some embodiments, the display generation component 103 also overlays generated acupuncture points 118 received from the central control server 136 on the 3D human body mesh of the patient 197 as shown on the display 103. In some embodiments, sensors data received from physiological sensors (e.g., sensors 116), user feedback sensors 124, and analysis results of the sensor data (e.g., received from the local site 102 or central server 136) are also displayed on display generation component 103 at the remote site 105.

In some embodiments, in addition to the display generation component 103, one or more input devices (e.g., a touch-sensitive surface, such as a touch-sensitive remote control, or a touch-screen display that also serves as the display generation component, a mouse, a joystick, a wand controller, a microphone 193 and/or cameras tracking the position of one or more features of the user (e.g., expert 108) such as the user's hands) is utilized by the remote expert 108 to provide inputs and instructions that will be utilized in guiding the treatment (e.g., controlling the robot 128 or directing the local operator 110). The one or more input devices include a haptic-enabled input device 111 (e.g., a three-dimensional haptic-enabled pointing device, a haptic-enabled glove, etc.) that generates force, motion, and/or texture feedback to the hand(s) of the remote expert 108 in accordance with simulated physical characteristics and physical interactions that occurs at a location on the 3D human body mesh of the patient's body 197 that corresponds to the current movement and position inputs provided via the input device 111. For example, when the movement and position inputs provided via the input device 111 corresponds to movement along a simulated surface on the 3D human body mesh of the patient's body 197 corresponding to the patient's shoulder, the haptic feedback generated on the haptic-enabled input device 111 will elicit haptic sensations in the user's hands that correspond to the shape, size, friction, texture, and hardness of the patient's shoulder. The real-time haptic feedback in conjunction with the visual rendering of the virtualized version of the patient's body allows the remote expert 108 to accurately experience and assess the problem site on the patient's body, and to provide more accurate and prudent guidance on the patient's treatment procedures.

In some embodiments, the input devices at the remote site 105 optionally support teleoperation as well, and the expert 108 can temporarily take over control of the robot arms 130 (using precise direct movement control that will be replicated by the robot, as opposed to command type control that is interpreted by the robot and executed based on pre-established task execution instructions) and perform the treatment at the desired locations on the patient's body based on images received from the local site. At other times, the remote expert allows the robot to operate fully autonomously according to pre-established task execution instructions after the remote expert has provided the remote guidance required to start the treatment procedures.

In some embodiments, the human operator 108 uses the haptic-enabled input device 111 to interact with virtualized surfaces on the 3D human body mesh of the patient's body 107, and mark the virtualized version of the patient's body with acupuncture points or adjust the locations of the automatically generated acupuncture points. In some embodiments, when new acupuncture points are specified by the remote expert, and/or when locations of the automatically generated acupuncture points are adjusted by the remote experts, the locations of the new acupuncture points and the adjusted locations of the acupuncture points are transmitted to the central control server 136, and the central control server 136 correspondingly update the display and projector instructions sent to the remote and local sites.

In some embodiments, the remote expert can use the haptic-enabled input device to mark a path for massages on the virtualized version of the patient's body. The path is provided to the central control server and relayed to the robot or displayed on the display located at the local site 102, which is then implemented during the treatment procedure.

In addition to the equipment collocated with the patient 104 (e.g., patient-side computing device 114) and the equipment (e.g., expert-side computing device 115) collocated with the remote expert 108, the remotely guided physical treatment environment 100 includes a central computing device (e.g., the central control server 136) that handles the extensive computation tasks related to visual and haptic data processing and rendering, generating the virtualized 3D human body mesh for the patient and generating the acupuncture points for the virtualized 3D human body mesh, updating the 3D human body mesh and tracking the acupuncture points in accordance with movement of the patient in the captured 2D image, and updating the acupuncture points based on expert input or feedback from the local site (e.g., sensors on the projectors), and generating treatment procedures and treatment plans with intermediate level instructions and workflows that bridge the gap between the high-level instructions from the remote expert and the low-level instructions executable by the robot. The central control server 136 is connected to the local site equipment 114 and/or the remote site equipment 115 via one or more networks 134. In some embodiments, the central control server 136 is collocated with the robot 128. In some embodiments, the central control server 136 is collocated with the remote expert 108. In some embodiments, the central control server 136 is not collocated with either the robot 128 or the remote expert 108.

In some embodiments, the central control server 136 handles the computation related to real-time, simultaneous localization and mapping (SLAM) using real-time dense surface mapping and tracking techniques, such as Kinect-Fusion. In some embodiments, other real-time three-dimensional modeling methods, e.g., Skinned Multi-Person Linear (SMPL) model, are used to generate a virtualized three-dimensional or pseudo-three-dimensional representation of the patient (e.g., the 3D human body mesh) based on the 2D image 107 captured at the local site 102. In some embodiments, the central computing device also performs haptic render and physics simulation for interactions between the remote expert and the virtualized version of the patient's body, e.g., via a virtual pointer. In some embodiments, the virtualized version of the patient's body is represented by a three-dimensional mesh that includes simulated surfaces that correspond to physical surfaces of the patient's body.

In some embodiments, the central control server 136 implements an image processing model (e.g., a human body recovery model) that has been trained on annotated data (e.g., ground truth data) from 2D and/or 3D images of patients varying in shape and poses, where the annotation data includes shape, poses, and locations of acupuncture points on the patient's bodies of different shapes, sizes, and other visual characteristics. When the model training is completed, the model is used to process a 2D image of the current patient, and reconstructing a 3D human body mesh of the patient's body, as well as parameters that are used to determine the locations of the acupuncture points on the patient's body. In some embodiments, once the new acupuncture points are generated for the patient's body, the locations of the acupuncture points are continuously tracked as the patient's body moves or changes posture, or as the imaging sensors change position to capture a different portion of the patient's body (e.g., from an upper portion to a lower portion of the patient's body). More details of generating the 3D human body mesh with the acupuncture points are described with respect to FIG. 3.

Figure 5:
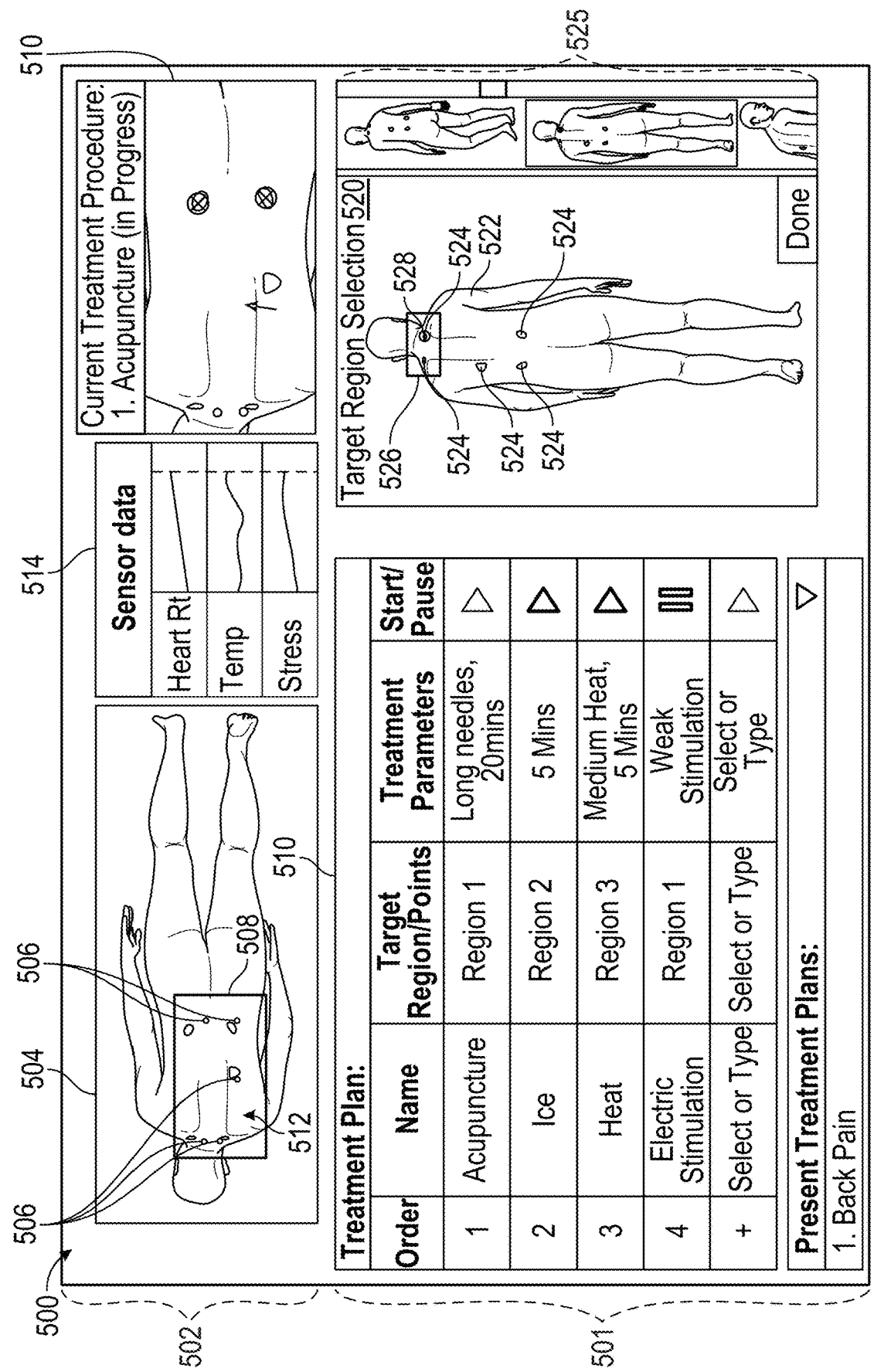
FIG. 5 illustrates an exemplary user interface for providing remote guidance for treatment of a patient by a remote expert, in accordance with some embodiments.

In some embodiments, the central control server 136 includes a treatment planner that generates a set of treatment procedures and treatment actions for each treatment procedure based on the acupuncture points and the input from the expert 108 (e.g., input provided via the user interface 500 shown in FIG. 5). The treatment planner takes into account both the characteristics of the patient's body, symptoms, locations of the acupuncture points, the input of the remote expert, and the feedback detected during the treatment procedures and/or earlier treatment procedures, and generates and modifies the treat plan in accordance with preprogrammed treatment planning instructions.

In some embodiments, the central control server 136 includes one or more of the following modules to implement its functions: a 3D Human Body Recovery Model 138 (e.g., including a 3D regression module, which further includes a discriminator module), a Model Training Module 140, an Acupuncture Points Generating Module 142, a Sensor Fusion and Analysis Module 144, a Treatment Plan Generation Module 146, a Remote Robotic Control Module 148 which further includes a Remote Guidance Module 150 and a Teleoperation Module 152, a Visual and Haptic Rendering Module 154, a Local Site User Interface Module 156, and a Remote Site User Interface Module 158.

Figure 2:
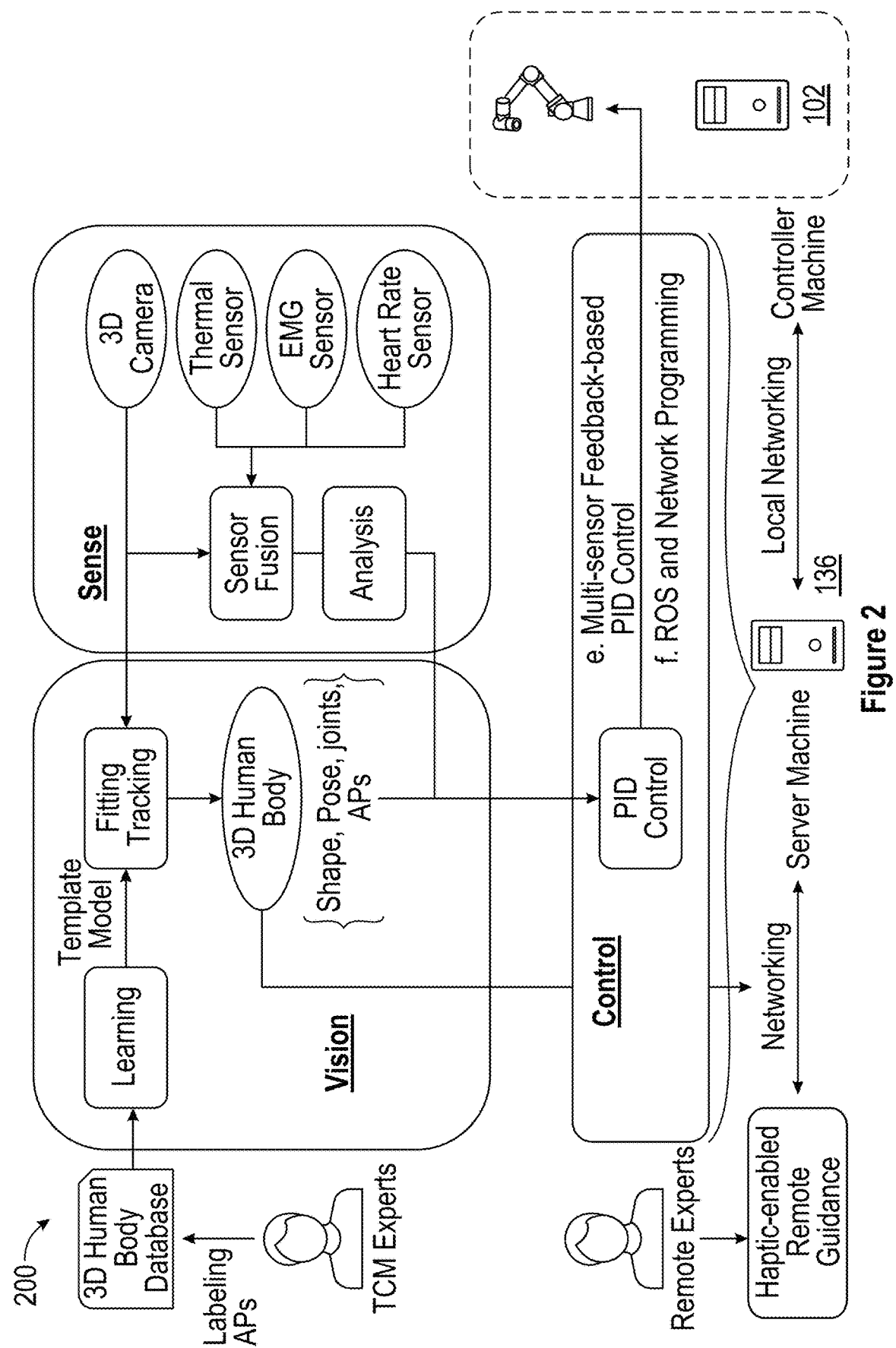
FIG. 2 is a block diagram illustrating an exemplary architecture that includes the remotely-guided treatment environment in accordance with some embodiments.

FIG. 2 is a block diagram illustrating an exemplary architecture 200 that includes the remotely-guided treatment environment 100 in accordance with some embodiments. As described herein, a key component of the treatment environment is automatic generation of acupuncture points based on the patient's 2D image and continued tracking of the acupuncture points during treatment when the patient moves or changes his/her postures, or the imaging sensors capture a different portion/segment of the patient.

In some embodiments, in order to establish a human body recovery model for generating customized acupuncture points for the current patient, a 3D human body mesh database is first established. 2D images of patients of various sizes, shapes, fitness levels, genders, ages, ethnicities, etc. are annotated by experts in physical treatment (e.g., traditional Chinese medicine experts, or physical therapists, experienced chiropractors, acupuncturist, massage therapists, etc.) to indicate locations for acupuncture points and/or other types of key physical points (e.g., muscles, joints, trigger points, etc.) relevant to various types of treatment procedures (e.g., acupuncture, electric stimulation, compression, acupressure, etc.) on the images. In some embodiments, the 2D images of the patients are analyzed to reconstruct 3D human body mesh of the patients and the acupuncture points are generated on the 3D human body mesh. In some embodiments, the 2D images are also labeled with various parameters that characterizes the visual characteristics of the patient's body in the images. The parameters include shape (e.g., actual shape or predefined categories of shapes) and sizes (e.g., general size, or actual dimensions) of various key parts of the human body (e.g., head, face, ears, neck, shoulder, lower back, abdomen, back, buttocks, left thigh, right thigh, left knee, right knee, left calf, right calf, left hand, right, hand, left wrist, right wrist, left foot, right foot, left sole, right sole, etc.). Other shape parameters optionally include muscle definition, fat content, swollenness, bruising, etc. In some embodiments, the images are also labeled with one or more pose parameters for the patients in the images. For example, the pose parameters include overall pose of the patient, such as sitting, lying facing down, lying facing up, lying sideways facing left, lying sideways facing right. Other pose parameters may be related to particular portions of the body, such as left leg bend to 45 degrees, arms on the side of torso, left arm raised up, head turn to the left side, eyes closed, etc. Annotations that are particular to certain parts of the body that are relevant to treatment as well as posture of the patient's body includes location and identities of joints, such as joints on the knees, hips, ankles, toes, writs, fingers, shoulders, spine, etc. Acupuncture points related to different health aspects, such as sleep, digestion, energy level, heart, liver, etc. are also annotated on the images. In some embodiments, the acupuncture points are optionally further annotated with the body functions that are related to the acupuncture points.

As described herein, reconstruction of a representation of the three-dimensional physical space in which the robot is operating needs to be performed in real-time with fair degree of accuracy in order for the user to provide appropriate and timely intervention. In order to facilitate real-time three-dimensional exploration, segmentation, marking, and interactions with the environment, haptic-rendering and physics simulation need to be performed in real-time in conjunction with the visualization of the environment.

Once a training database is established with annotated images of the patients. The images and annotation data are used in training an human body recovery model. In some embodiments, shape and pose parameters of the current patient are extracted from the 2D image and used to customize (e.g., deform, adjust) a 3D human body template in accordance with the relevant parameters of the patient with locations of acupuncture points. In some embodiments, a discriminator module is trained using 2D and/or 3D ground truth data for evaluating whether the parameters in the reconstructed 3D human body mesh and whether the acupuncture points correspond to a real human body.

As shown in FIG. 2, sensor data from various sensors (e.g., image sensors (e.g., 3D images, infrared images, etc.), thermal sensors (e.g., temperature sensors, infrared sensors on the robot arms, etc.), physiological sensors (e.g., EMG sensors, heart rate sensors, etc.), patient feedback sensors (e.g., pressure sensors, microphone), etc.) are merged based on time (e.g., correlated based on the same or similar timestamps of the sensor data) and grouped based on indicator type (e.g., related to pain, stress, comfort, etc.) through a sensor fusion process, and the fused sensor data is analyzed and provided to the central control server 136 to be output as visual indications for various types of measures for determining whether the treatment is effective, comfortable, and/or painful to the patient, and how the treatment parameters may be adjusted to improve the effectiveness, comfort level, and tolerance level of the patient.

As shown in FIG. 2, the generated acupuncture points are provided to the central control server 136 and passed to the remote site (and optionally to the local site) for display. In some embodiments, the central control server 136 generates a 3D human body mesh of the patient's body. In some embodiments, the 3D human body mesh is generated in accordance with the shape and pose parameters of the patient.

As shown in the FIG. 2, the remote expert interacts with the reconstructed 3D human body mesh of the patient and optionally adjusts the locations of the acupuncture points through a user interface displaying the 3D human body mesh and the acupuncture points. In some embodiments, the interaction is provided with a haptic enabled device such that the remote expert can experience the surface of the 3D human body mesh with real size, shape, and texture feedback. In some embodiments, the remote expert selects a subset of the acupuncture points as target points for a selected treatment procedure. In some embodiments, the remote expert demonstrates the treatment procedure on the virtual three-dimensional model, such that the same procedure can be performed by the local operator, the patient, or the robot at the local site. In some embodiments, the remote expert specifies a sequence of treatment procedures, and also interact with the patient, and/or the local operator to inquire about the patient's symptoms, asking the patient or operator to adjust the patient's posture, and explain the treatment procedure and their purposes to the patient.

In some embodiments, the treatment plan including the treatment procedures and the locations of the acupuncture points targeted by the treatment procedures are sent to the robot located at the local site. The robot implements the treatment plan and performs the treatment procedures according to the locations of the acupuncture points and the instructions in the treatment plan. In some embodiments, the robot returns local feedback sensor data to the central control server, and the central control server continues to update the 3D human body mesh of the patient's body, the locations of the acupuncture points, and the sensor data received from the local site, and send the updated data to the remote site, for the remote expert to update the treatment plan or treatment parameters for the treatment procedures included in the treatment plan accordingly.

FIG. 2 is merely an illustration of an exemplary architecture of a treatment environment. Other structure of the architecture is possible, and the architecture may include other components and communication routes, as will be apparent to the skilled person based on the present disclosure.

FIG. 3 illustrates an exemplary processing pipeline 300 for reconstructing a three dimensional (3D) mesh of a human body directly from a single two dimensional (2D) image. In some embodiments, the processing pipeline 300 includes training and using a 3D reconstruction model for reconstructing a 3D mesh of a human body and showing acupuncture points on the reconstructed 3D mesh of the human body. In some embodiments, the processing pipeline further includes training and applying a 3D regression model to the reconstructed 3D mesh with the corresponding acupuncture points to obtain a minimized combined loss.

In some embodiments as discussed with reference to FIG. 1A, the imaging sensor 106 at the local site 102 captures a two-dimensional (2D) image of at least a portion of a human subject 104. In some embodiments, the captured 2D image is a single RGB image centered on a human body or a portion of a human body. For example, the captured 2D image is a full-body image of the human subject 104, an image of an upper body of the human subject 104, an image of a lower body of the human subject 104, or a significant portion of the human body for which posture change is sufficiently discernable.

In some embodiments, a plurality of 2D annotated images, a pool of 3D meshes of human bodies of varying shapes and poses, and 3D datasets including 3D data of acupuncture points marked on respective 3D meshes of human bodies are provided (310). In some embodiments, the 2D annotated images include images captured by cameras that are further annotated with 2D keypoints. In some examples, the keypoints include various physical key points of a human body, such as one or more joints on the human body, or one or more facial keypoints. In some embodiments, the pool of 3D meshes of human bodies include 3D datasets of 3D meshes of people with various shapes (e.g., related to height, weight, and/or body proportions of a human body, various segments/portions of a human body) and/or poses (e.g., including one or more common poses of a patient receiving acupuncture treatment on a treatment table). In some embodiments, the 3D datasets include 3D data (e.g., location data) of acupuncture points that are collected using a 3D scanner with marker to show the acupuncture points on respective 3D human bodies. In some embodiments, the 3D datasets are collected by requesting doctors (e.g., Traditional Chinese Medicine (TCM) doctors) to label acupuncture points on one or more 3D human body models, and the 3D datasets store 3D data (e.g., location data) of the acupuncture points labeled on the corresponding 3D human body models. In some embodiments, the TCM doctors are provided with 3D human body models of various shapes, heights, poses, weights, ages, and/or sexes for labeling the acupuncture points. In some embodiments, the TCM doctors are requested to label corresponding acupuncture points on one or more segments/portions of 3D human body models, such as an upper body of the 3D human body, a lower body of the 3D human body, a head of the 3D human body, a limb (e.g., an arm, a leg, a feet) of the 3D human body.

In some embodiments, the computing system (e.g., the local computing device 114, or the central control server 136, FIG. 1A) obtains (320) a single captured 2D image for further processing as discussed herein in method 300. In some embodiments, the computing system further processes (320) the captured 2D image to obtain various image features $\phi$ (e.g., convolutional features) from the 2D image for reconstructing a three-dimensional (3D) human body mesh in the following steps. For example, the computing system uses a trained model (e.g., a deep neural network model including multiple layers, such as ResNet 50) to obtain the convolutional features of the captured 2D image.

In some embodiments, the computing system further processes (330) the captured 2D image using a trained human body recovery model to reconstruct a 3D human body mesh of the human subject with acupuncture points. For example, the trained human body recovery model includes a Skinned Multi-Person Linear (SMPL) model that is used for outputting a 3D mesh of a human body. In some embodiments, the human body recovery model reconstructs the 3D human body mesh based on a plurality of parameters including human body parameters related to shape (($\beta$) (e.g., height, weight, body proportions), pose ($\theta$), acupuncture points ($\alpha$) of the human subject, and camera parameters (e.g., global rotation, translation, scale) for taking the 2D image. In some embodiments, the human body recovery model reshapes a 3D body mesh template based on the shape and pose parameters of the human subject. In some embodiments, the human body recovery model further projects (e.g., orthographic projection) key physical points (e.g., joints, facial keypoints) and acupuncture points onto the reconstructed 3D human body mesh. In some embodiments, the human body recovery model includes a plurality of human body recovery sub-models corresponding to a plurality of portions of a human body respectively (e.g., such as an upper body, a lower body, a head, a limb, etc.).

In some embodiments, the shape parameter $\beta$ is related to how human individuals vary in height, weight, body proportions, etc. In some embodiments, the shape parameter $\beta$ is parameterized by a plurality of coefficients of a principal component analysis (PCA) shape space. In some embodiments, the pose $\theta$ articulates how the 3D surface of the human body mesh deforms in accordance with the distribution of the physical key points and different poses of the corresponding physical key points. In some embodiments, the pose $\theta$ is modeled by relative 3D rotation of a number of key physical points, such as a number of joints (e.g., K joints) in axis-angle representation (e.g., $\theta \in R^{3K}$). In some embodiments, the acupuncture points $\alpha$ includes a plurality of location parameters (e.g., in 2D plane and/or in 3D dimension) corresponding to respective location information of a plurality of acupuncture points on a 3D human body.

In some embodiments, the human body recovery model includes a differentiable function that outputs a triangulated (triangle) mesh with N vertices $M(\theta,\beta) \in R^{3 \times N}$. In some embodiments, the triangulated mesh M is obtained by shaping a template body vertices conditioned on shape $\beta$ and pose $\theta$ of the human subject, followed by articulating the bones according to the joint rotations $\theta$ via forward kinematics, and deforming the surface with linear blend skinning.

In some embodiments, respective location information of a plurality of acupuncture points α are estimated in accordance with the shape β, pose θ, and location of one or more physical key points. In one example, the location information of the acupuncture points α are determined on the 3D human body mesh (e.g., the mesh M) according to predetermined location relationship between one or more acupuncture points and one or more key physical points (e.g., joints, facial feature points, or other human body feature points). In another example, the acupuncture points α are determined on the 3D human body mesh (e.g., the mesh M) in accordance with 3D datasets of the acupuncture points that are obtained from 3D scanner or TCM doctor annotations on 3D human body models as discussed herein. In some embodiments, a plurality of 3D key physical points that are used for calculating reprojection error $X(\theta,\beta) \in R^{3 \times P}$ in the following steps are obtained by linear regression from the final mesh vertices.

In some embodiments, the plurality of parameters of the 2D image include one or more camera parameters such as global rotation R, translation t, and scale s. In some embodiments, the human body recovery model further includes a camera model used for obtaining the camera parameters including the global rotation R in axis-angle representation, translation t, and scale s. In some embodiments, the plurality of camera parameters that represent the 3D reconstruction of a human body mesh is expressed as a multiple-dimensional vector (e.g., $\Theta = \{\theta, \beta, \alpha, R, t, s\}$). In some embodiments, the projection of an acupuncture point $X(\theta,\beta)$ is calculated based on the camera parameters, e.g., $\hat{x} = s\Pi(RX(\theta,\beta))+t$, where $\Pi$ is an orthographic projection (e.g., representing 3D objects in 2D dimension). In some embodiments, one or more key physical points are also respectively projected (e.g., the orthographic projection) onto the 3D human body mesh based on the camera parameters.

In some embodiments, the computing system performs (340) iterative 3D regression to output a 3D human body mesh with a minimized combined loss. In some embodiments, the iterative 3D regression is performed for a predetermined iteration times T (e.g., T=3, 5, 10, 20, or 100, etc.) to train the 3D human body recovery model for reconstructing (e.g., outputting) the 3D human body mesh with corresponding acupuncture points. In some embodiments, the 3D regression model is supervised to achieve the minimized combined loss $L = \lambda(L_{reproj} + L_{3D}) + L_{adv}$, where $L_{reproj}$ includes acupuncture points reprojection error/loss, $L_{3D}$ represents 3D losses, and $L_{adv}$ is adversarial loss for verifying whether the obtained 3D human body mesh with corresponding acupuncture points correspond to real human shape, pose, and acupuncture points. In some embodiments, the $L_{reproj}$ further includes physical key points reprojection error/loss. In some embodiments, the 3D regression is performed to train the 3D human body recovery model until the combined loss L is reduced to a preset loss value. In some embodiments, each acupuncture point is trained and then the computing system integrates all the acupuncture points together to output a 3D human body mesh based on the physical key points and marked with acupuncture points with a minimized combined loss L.

In some embodiments, the iterative regression is performed in an iterative error feedback loop, where progressive changes are made recurrently to the current estimate. In some embodiments, the trained 3D regression model for reconstructing the 3D human body mesh takes the image features φ of the captured 2D image (e.g., at step 320) and the plurality of parameters Θ (e.g., as discussed in step 330) as input to the 3D regression model, and the 3D regression model outputs a change of the parameters ΔΘ of the current loop. The parameters as the input of the next loop $\Sigma_{t+1}$ are updated by adding the change of the parameters ΔΘ to the parameters $\Theta_t$ of the current loop (e.g., $\Theta_{t+1} = \Theta_t + \Delta\Theta$).

In some embodiments, the reprojection loss/error ($L_{reproj}$) is related to collective projection errors of respective acupuncture points and other types of key physical points during the generation of the 3D human body mesh including 3D projections from the 2D key physical points locations, such as:

$$L_{reproj} = \Sigma_i \|v_i(x_i - \hat{x}_i)\|_1$$

where $x_i$ is the $i^{th}$ ground truth 2D data of the acupuncture point or another type of physical key point (e.g., annotated on the 2D image), $\hat{x}_i$ is the projection of the corresponding $i^{th}$ acupuncture point or the physical key point based on the camera parameters as discussed above, and $v_i$ represents visibility (e.g., 1 if visible, 0 if not visible) of the corresponding $i^{th}$ acupuncture point or the physical key point. In some embodiments, the iterative 3D regression is performed to output the 3D human body mesh based on the image features obtained from the captured 2D image such that the joint reprojection error $L_{reproj}$ is minimized. In some embodiments, the reprojection loss/error ($L_{reproj}$) includes collective projection errors (e.g., a sum) generated from projecting respective acupuncture points and respective physical key points obtained from 2D features to the reconstructed 3D human body mesh.

In some embodiments, 3D supervision is performed when 3D ground truth data are available. In some embodiments, the 3D losses $L_{3D}$ is a 3D ground truth error related to 3D key physical points losses ($L_{3D\ points}$), 3D shape and pose losses ($L_{3D\ smpl}$), and 3D acupuncture point losses $L_{3D\ AP}$. For example, the 3D losses $L_{3D}$ is a sum of $L_{3D\ points}$, $L_{3D\ smpl}$ and $L_{3D\ AP}$.

In some embodiments, the 3D key physical points losses $L_{3D\ points}$ can be calculated when 3D ground truth data for the key physical points are available, e.g., 3D annotation of the key physical points are available (e.g., from standard database or annotation by TCM doctors). In some embodiments, the 3D key physical points losses $L_{3D\ points}$ are determined by a comparison between the 3D ground truth data of a key physical point and projection of the corresponding key physical point based on the camera parameters (e.g., $L_{3D\ point-i} = \|X_i - \hat{X}_i\|_2^2$).

In some embodiments, the 3D shape and pose losses ($L_{3D\ smpl}$) are obtained when ground truth data of the shape and pose parameters that are used in the SMPL model for 3D human body mesh reconstruction are available. For example, the 3D shape and pose losses ($L_{3D\ smpl}$) are determined as $L_{3D\ smpl} = \|[\beta_i,\theta_i] - [\hat{\beta}_i, \hat{\theta}_i]\|_2^2$.

In some embodiments, the 3D acupuncture point losses $L_{3D\ AP}$ are obtained using the 3D datasets including ground truth 3D data of acupuncture points marked on respective 3D meshes of human bodies as discussed with reference to step 310 of method 300. In some embodiments, the 3D acupuncture point losses $L_{3D\ AP}$ are determined as $L_{3D\ AP} = \|d_i - \hat{\alpha}_i\|_2^2$. In some embodiments, the 3D acupuncture point losses include a plurality of sub-losses corresponding to respective acupuncture points.

In some embodiments, the adversarial loss ($L_{adv}$) (also referred to as a discriminator error) provides a measure of whether the obtained 3D human body mesh with corresponding acupuncture points correspond to real human shape, pose, and acupuncture points. In some embodiments, a discriminator network/module including a plurality of sub-discriminators are trained to determine the adversarial loss $L_{adv}$. In some embodiments, each acupuncture point corresponds to an individual sub-discriminator for determining the respective adversarial loss of the corresponding acupuncture point (e.g., the possibility of the corresponding acupuncture point corresponds to an acupuncture point on a real human). In some embodiments, sub-discriminators are independently trained for the shape and pose respectively. In some embodiments, a respective sub-discriminator is trained for each key physical point. In some embodiments, each sub-discriminator outputs a value between 0 and 1, representing the probability the corresponding parameter corresponds to a real human parameter. In some embodiments, the sub-discriminators are evaluated individually to optimize the result of each sub-discriminator, and jointly to optimize the performance of the image encoder for obtaining image features and the human body recovery model. In some embodiments, suitable statistics methods, such as least squares method, are used for the optimization process.

In some embodiments, the 3D key physical points losses $L_{3D\ points}$ and the 3D shape and pose losses $L_{3D\ smpl}$ are applied on the final estimate OT in the final loop. In some embodiments, the adversarial loss $L_{adv}$ is applied on the estimate at every iteration such that the 3D regression model can correct the estimate $\Theta_t$ based on the real human bodies at every iteration.

In some embodiments, the computing system outputs (350) a reconstructed 3D human body mesh (e.g., the 3D human body mesh 197, FIG. 1B) for the human subject. In some embodiments, the 3D human body mesh 197 is marked with acupuncture points (e.g., acupuncture points 118, FIG. 1B). In some embodiments, the computing system generates (360) treatment data associated with respective acupuncture points for the human subject in accordance with the reconstructed 3D human body mesh with acupuncture points corresponding to the human subject (e.g., as discussed with reference to FIGS. 1B and 2).

In some embodiments, a database of 3D human body meshes of patients' bodies are annotated with various types of parameters, including shape parameters, posture parameters, joints parameters, and locations of acupuncture points. The annotated 3D human body meshes are used in training to obtain a human body recovery model (e.g., including Skinned Multi-Person Linear (SMPL) model) for obtaining respective shape parameters, posture parameters, joint parameters, and acupuncture points that are representative of the human bodies represented in the training data. When a 2D image of a patient is received from a local site, the 2D image is processed to determine the body shape parameters, posture parameters, and acupuncture points parameters. In some embodiments, the posture parameters are manually entered or corrected by the patient or local operator. In some embodiments, the posture parameters are specified by the remote expert or the local operator, and the patient is positioned according to the specified posture parameters before the images of the patient are streamed. The shape, pose, and acupuncture points parameters are then used to shape a template body mesh vertices and articulate the physical key points on the customized 3D human body mesh. In some embodiments, a camera model and camera parameters are used to project acupuncture points and other types of physical key points from 2D feature datasets to the reconstructed 3D human body mesh. In some embodiments, 3D iterative regression model is used to further verify the generated 3D human body mesh and the acupuncture points. For example, the 3D iterative regression model is used to minimize a combined loss, including reprojection losses, 3D losses, and discriminator errors as discussed above in step 340. In some embodiments, the a discriminator module including a plurality of sub-discriminator respectively evaluate whether the shape, pose, and acupuncture points correspond to a real human body.

In some embodiments, during the treatment session, the patient may move slightly, and the movement of the patient causes the 2D image streamed to the control server to change slightly, resulting in changes in the shape parameters and locations of acupuncture points of the patient's body. If the changes are relatively small, e.g., smaller than preset threshold percentage, the reconstructed 3D human body mesh is not changed, and the locations of the acupuncture points are not changed. If the changes are relatively large, e.g., larger than the preset threshold percentage, the 3D human body mesh is reconstructed using the trained model based on the new shape and acupuncture points parameters derived from the updated 2D image. The locations of the acupuncture points are updated and verified based on the new locations of the acupuncture points using the 3D iterative regression model. In some embodiments, if the posture of the patient changed (e.g., the patient lifted his leg or turned sideways), or if the imaging sensors capture a different portion of the human body, the 3D human body mesh is reconstructed using the trained model based on the new shape and acupuncture points parameters derived from the updated 2D image. The locations of the acupuncture points are updated and verified based on the new locations of the acupuncture points using the 3D iterative regression model.

In some embodiments, when the locations of the acupuncture points generated for the patient are sent to the projector at the local site, and the projector projects light spots onto the patient's body based on the locations of the acupuncture points and the currently known shape and location of the patient's body, if the locations of the light spots do not align with the predicted locations of the acupuncture points on the patient's body, the differences are reported back to the central control server, and the central control server adjusts the reconstruction of the 3D human body mesh of the patient's body and the acupuncture points on the 3D human body mesh until the light spots and the predicted locations of the acupuncture points are sufficiently aligned at the local site.

Figure 4A:
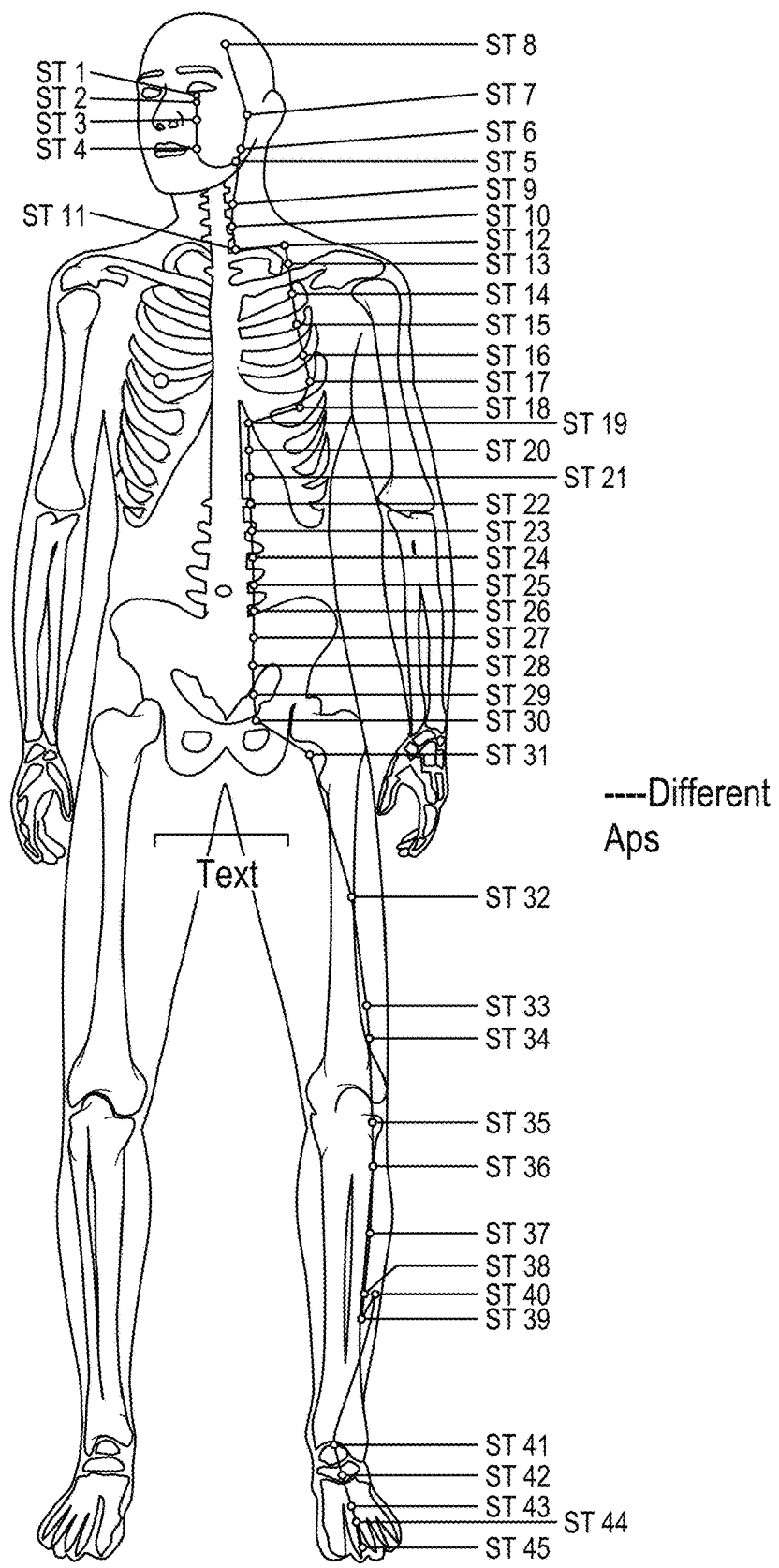
Figure 4C:
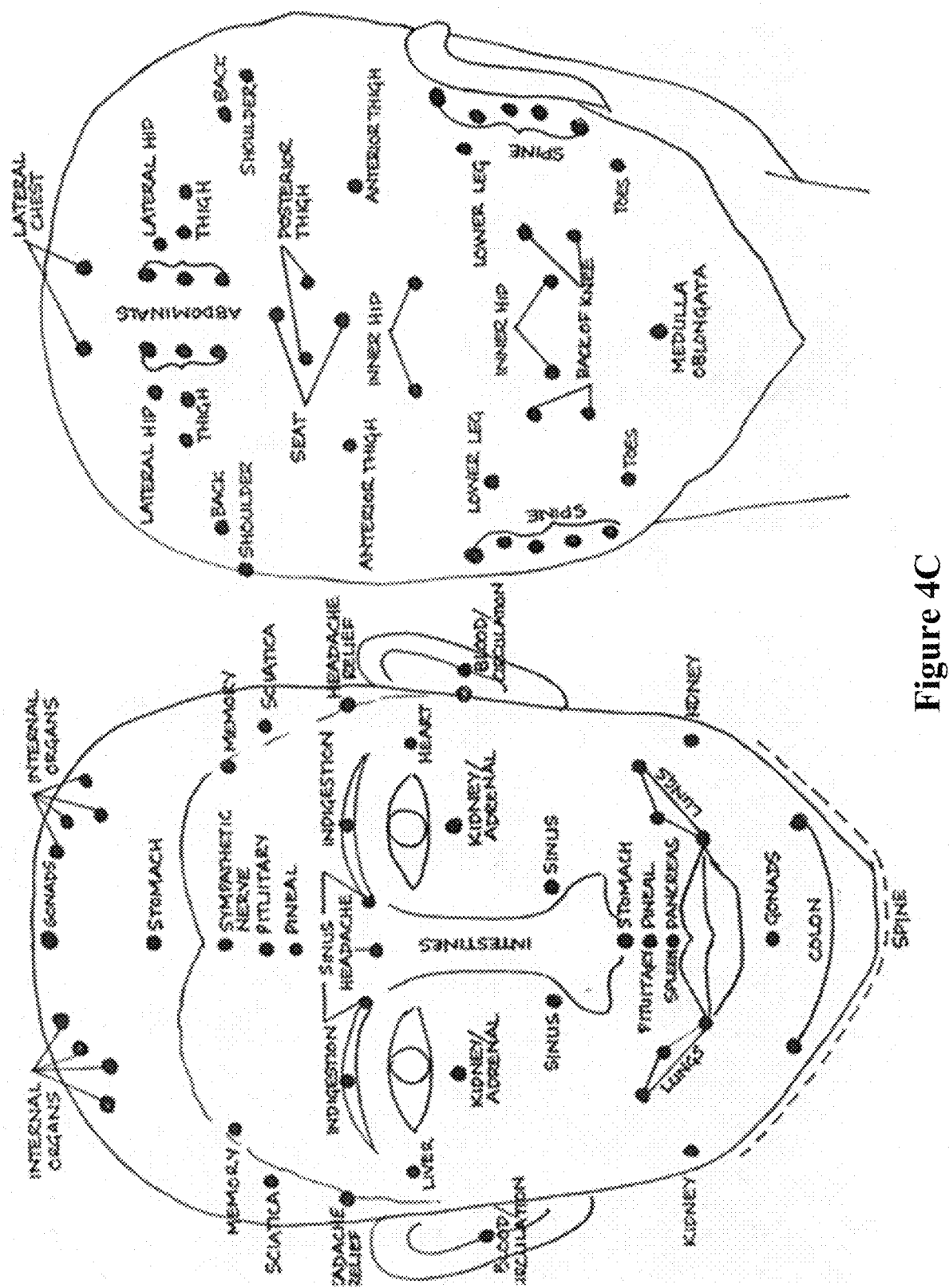
Figure 4D:
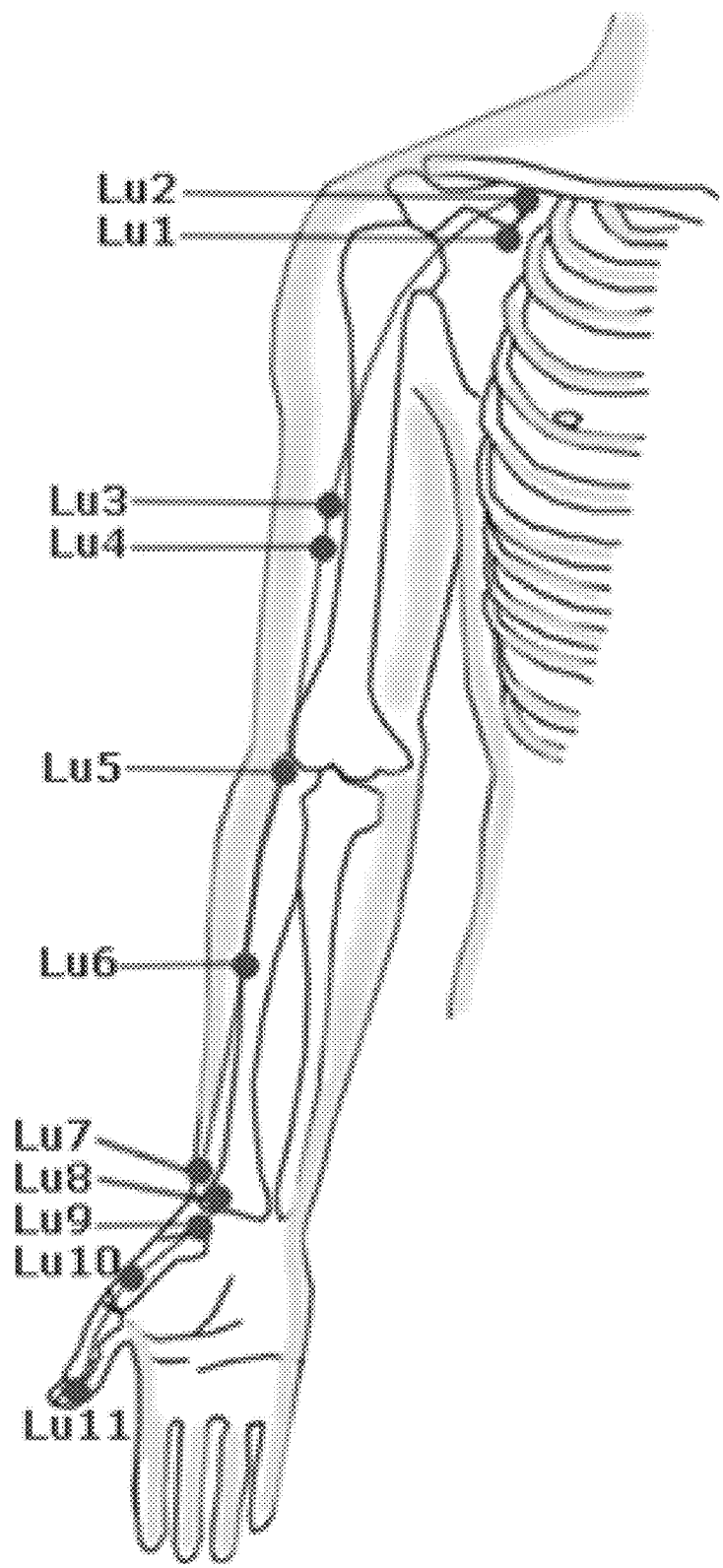
Figure 4E:
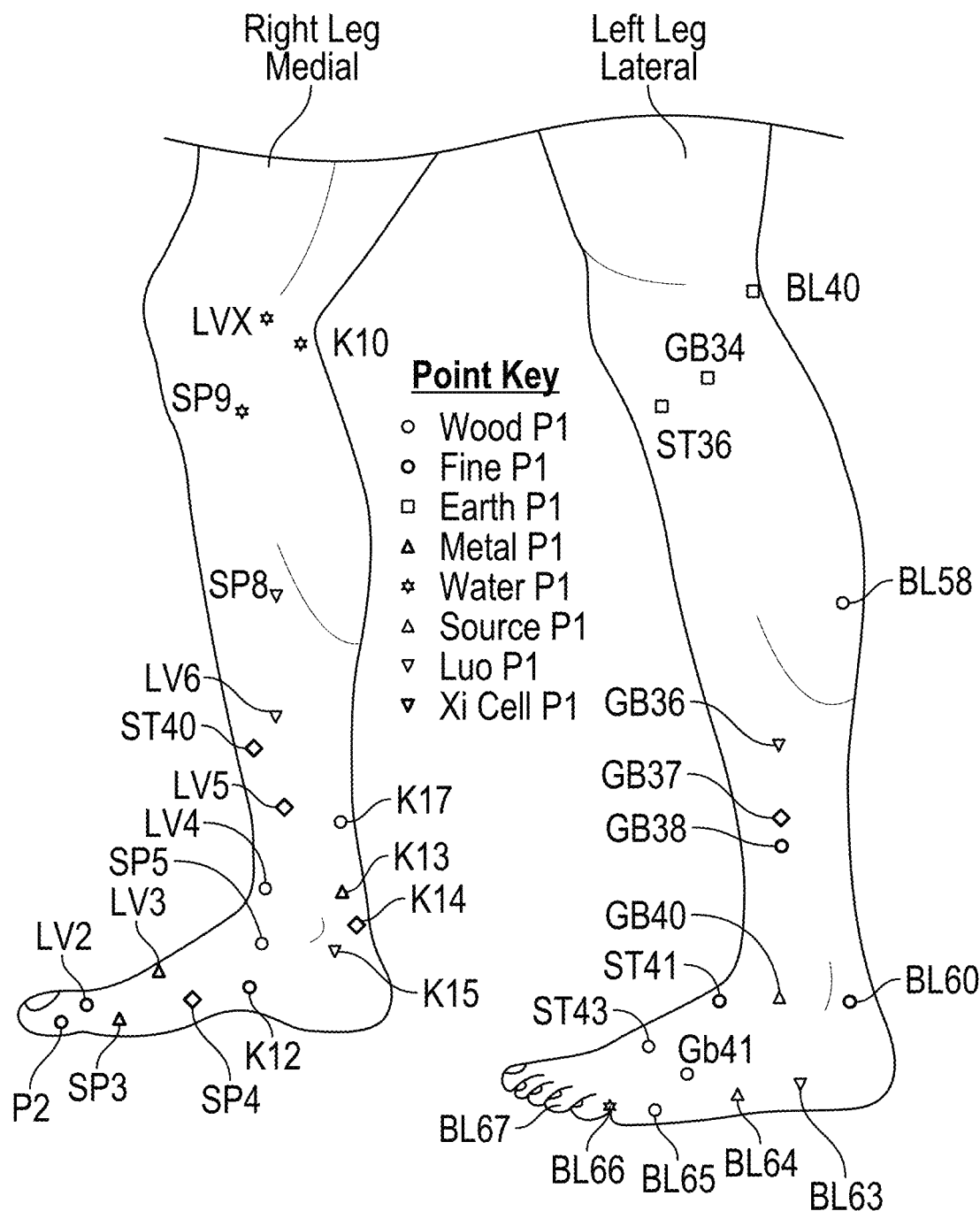

FIGS. 4(A)-4(E) illustrate exemplary 3D full-body map and acupuncture points maps, respectively (e.g., a full-body map in FIG. 4(A) and acupuncture points maps in FIGS. 4(B)-(E)) of various portions of a human body, in accordance with some implementations. In some embodiments, the location information (e.g., including 2D data and/or 3D data) of the acupuncture points on a human body as shown in FIG. 4(A) is regarded as ground truth data. In some embodiments, the ground truth acupuncture points data can be obtained using a 3D scanner with markers to show the acupuncture points on respective 3D human bodies. In some embodiments, the ground truth acupuncture points data can be obtained from annotation data labeled by the TCM doctors on 3D human body models varying in shapes, poses, and portions. In some embodiments, as discussed with references to FIG. 3, the trained the trained human body recovery model can reconstruct a 3D human body mesh, and provide acupuncture points on the 3D human body mesh. In some embodiments, the human body recovery model includes an iterative regression module for minimizing a 3D ground truth error which further includes acupuncture points estimation errors relative to annotated 3D acupuncture points data (either full-body acupuncture points data or subsets of acupuncture points on respective portions of a human body). In some embodiments, the human body recovery model includes a discriminator module for determining whether the reconstructed human body mesh (either full-body or partial) with corresponding acupuncture points correspond to real human body with acupuncture points. In some embodiments, the discriminator module includes a plurality of sub-discriminator corresponding to respective portions of a human body (e.g., such as ear in FIG. 4(B), head in FIG. 4(C), an arm in FIG. 4(D), and legs in FIG. 4(E)).

FIG. 5 illustrates an exemplary user interface 500 for providing remote guidance for treatment of a patient by a remote expert, in accordance with some embodiments. As shown in FIG. 5, the user interface 500 includes a real-time data display portion 502 and a treatment planning and adjustment region 501. In the real-time data display portion 502, a virtualized version of the patient's body 504 is displayed in a first region. In some embodiments, the virtualized version of the patient's body 504 is a 3D human body mesh surface representing the shape and pose of the patient's body on the support surface at the local site. In some embodiments, the acupuncture points 506 that are identified for the patient's body are overlaid on the virtualized version of the patient's body 504. In some embodiments, a target region selection window 508 is displayed overlaid on the virtualized version of the patient's body 504. The remote expert can slide the target region selection window 508 across different portions of the virtualized version of the patient's body and view them in the zoomed viewing region 510. By default, the window 508 is placed over a region of the virtualized version of the patient's body that is currently the target region of the currently executed treatment procedure. For example, during the treatment procedure, the remote expert can move the window 508 by dragging it using a virtual pointer 512, and the region of the patient's body within the window 508 will be displayed in zoomed viewing region 510. Once the remote expert releases the window 508, the window automatically goes back to the target region of the current treatment procedure, and the portion of the patient's body shown in zoomed viewing region 510 becomes the target region of the current treatment procedure. This user interface feature allows the remote expert to check on other portions of the patient's body during a treatment procedure, as if he or she is at the location of the patient. In some embodiments, the remote expert may temporarily lock the location of the window 508 after dragging it away from the default location by pressing a special key on the input device. In the zoomed viewing region 510, by default the status and progress of the current treatment procedure is shown. For example, as shown in FIG. 5, the currently executed treatment procedure is acupuncture on region 1 of the patient's body, with long needles, for 20 minutes. The zoomed viewing region 510 shows that two needles have been inserted into the five key physical points selected for the treatment procedure in region 1. As a new needle is inserted into the next key physical point, the key physical point will be highlighted as well (e.g., with a cross "x"). In some embodiments, the remote expert can explore the portion of the patient's body shown in the zoomed viewing region 510 using a haptic enabled input device. As virtual pointer 512 is dragged across the surface of the portion of the virtualized version of the patient's body shown in the zoomed viewing region 510, the central control computer provides haptic feedback to the expert's hand via the haptic enabled input device (e.g., device 111), such that the remote expert can experience the change in contour, texture, and stiffness of the patient's skin. The helps the remote expert better adjust the treatment procedure and the locations of the key physical points during the treatment procedure.

As shown in FIG. 5, sensor data from the local site is displayed in the sensor feedback display region 514. For example, patient's heart rate, temperature, stress level, etc. are shown in this region and are continuously updated during the treatment procedures. Some of these sensor data are raw sensor data, and some are aggregated sensor data. In some embodiments, some of the data is analysis results derived based on a combination of multiple types of sensor data. For example, stress level is a type of data that is derived from physiological responses (e.g., blood pressure, heart rate, perspiration, muscle tension, etc.) as well as other active user feedback data (e.g., pressure sensor on the user's hand, user's verbal communication, user's facial expression, etc.). The remote expert optionally selects the types of sensor data that he/she wants to display in this region, to determine the suitable treatment procedures. For example, if the purpose of the treatment is relaxation, the remote expert will place relevant sensor data for determining stress levels in display region 514. If the purpose of the treatment is pain reduction, the remote expert will place relevant sensor data for determining pain and discomfort in display region 514. In some embodiments, the user interface allows the remote expert to select a purpose for the treatment, and automatically populates the sensor data types into the sensor feedback display region 514.

In the user interface 500, treatment plan input region 510 is not dynamically updated in real-time. In the treatment plan specification region 510, the remote expert has selected multiple treatment procedures that are to be carried out in a current treatment session. In some embodiments, the treatment plan can be started, even before all of the treatment procedures have been specified. Sometimes, the later treatment procedures are determined by the remote expert based on the result of the earlier performed treatment procedures. For example, in the current treatment plan, the first treatment procedure is specified to be "acupuncture", and the user interface allows the remote expert to select a target region on the patient's body for each treatment procedure. After the target region for the treatment procedure is specified, the user interface allows the remote expert to select one or more treatment parameters for the treatment procedure. Once all the treatment parameters are specified, a control is displayed for the remote expert to send a command to start the treatment procedure. As shown in FIG. 5, the user interface 500 shows that the remote expert has specified three treatment procedures completely. The first treatment procedure is acupuncture, and it is to be applied to region 1 of the patient's body. In some embodiments, during the specification of the target region, the remote expert can select particular subset of key physical points in the target region of the patient's body as the target points for the treatment procedure. In some embodiments, the remote expert is also given a way to specify the order by which these target points are to be manipulated in the treatment procedure. In the treatment parameter region, the remote expert can specify the equipment needed (e.g., long needles) and the time required for each needle to remain inserted (e.g., 20 minutes). In this particular example, the acupuncture procedure has been started by the remote expert (e.g., as indicated by the "paused" button shown next to the first treatment procedure). If the remote expert wishes to stop the current treatment procedure before it is completed (e.g., due to patient's discomfort indicated by the sensor data), the remote expert can activate the pause button next to the first treatment procedure. The robot located at the local site will stop the treatment procedure according to the command received from the remote expert.

As illustrated in FIG. 5, in this example, the remote expert has started/paused to specify a first treatment procedure (e.g., acupuncture) in the treatment plan. The expert has selected a target region (e.g., region 4 (e.g., user's neck region)) of a virtualized version of the patient's body 522 shown in a target selection region 520. As shown in FIG. 5, the remote expert can select a posture for the treatment procedure from a listing of possible postures 525 (e.g., lying facing downward, lying with left leg slightly bent, lying on the left side with both legs slightly bent, etc.). In some embodiments, once the remote expert has selected a posture for the treatment procedure, the selected posture is shown in the target selection region 520 in an enlarged state. The key target points (e.g., acupuncture points) for the patient's body are displayed on the three-dimensional human body mesh shown in the target selection region. In some embodiments, the model shown in the target selection region 520 is the reconstructed 3D human body mesh generated from the patient's 2D image captured at the local site (as discussed with reference to FIG. 3). In some embodiments, the posture of the 3D human body mesh shown in target region selection region is adjustable in response to the remote expert's input. For example, the remote expert can drag the mesh's leg to bend it, or move the mesh's arm to raise it above the mesh's head, etc. In some embodiments, once the mesh's posture is adjusted, the adjusted mesh posture is sent to the local site, and the patient or local operator can help the patient to adjust the patient's posture accordingly before the corresponding treatment procedure is started.

In the target selection region 520, the acupuncture points 524 are shown overlaid on the 3D human body mesh of the patient's body. The remote expert can select a region by placing a resizable box 526 over a region on the model. The remote expert can also select particular acupuncture points (e.g., point 528) within the selected target region to be the target points of the treatment procedure. Once all the target region is selected, the remote expert can select the "done" button in the target selection region to enter the information of the target region and target points into the target region portion of the treatment procedure 1 "acupuncture." Once the expert has also selected the treatment parameters, e.g., acupuncture, etc. for the treatment procedure, a control is enabled (e.g., a start button is displayed) for starting the treatment procedure.

In some embodiments, the user interface 500 provides preset treatment plans for the remote expert to select for a particular patient. In some embodiments, the user interface 500 allows the remote expert to save the current treatment plan once it is fully specified or fully completed. In some embodiments, after a saved or preset treatment plan is selected, and the treatment procedures and corresponding parameters are populated in the treatment plan specification region, the remote expert can still modify particular aspects of the treatment plan, in the same manner as outlined above, using the user interface 500.

In some embodiments, requiring the patient to be still during the treatment and tracking and predicting user's movement based on the manipulation being applied, helps to reduce issues with network latency as well. In some embodiments, if too much movement is detected during a treatment procedure, an alert is generated on the user interface 500, and the remote expert can enter a command in the user interface 500 to request the treatment procedure to be performed again and require the robot to restrain the movement of the patient during the procedure.

Figure 6:
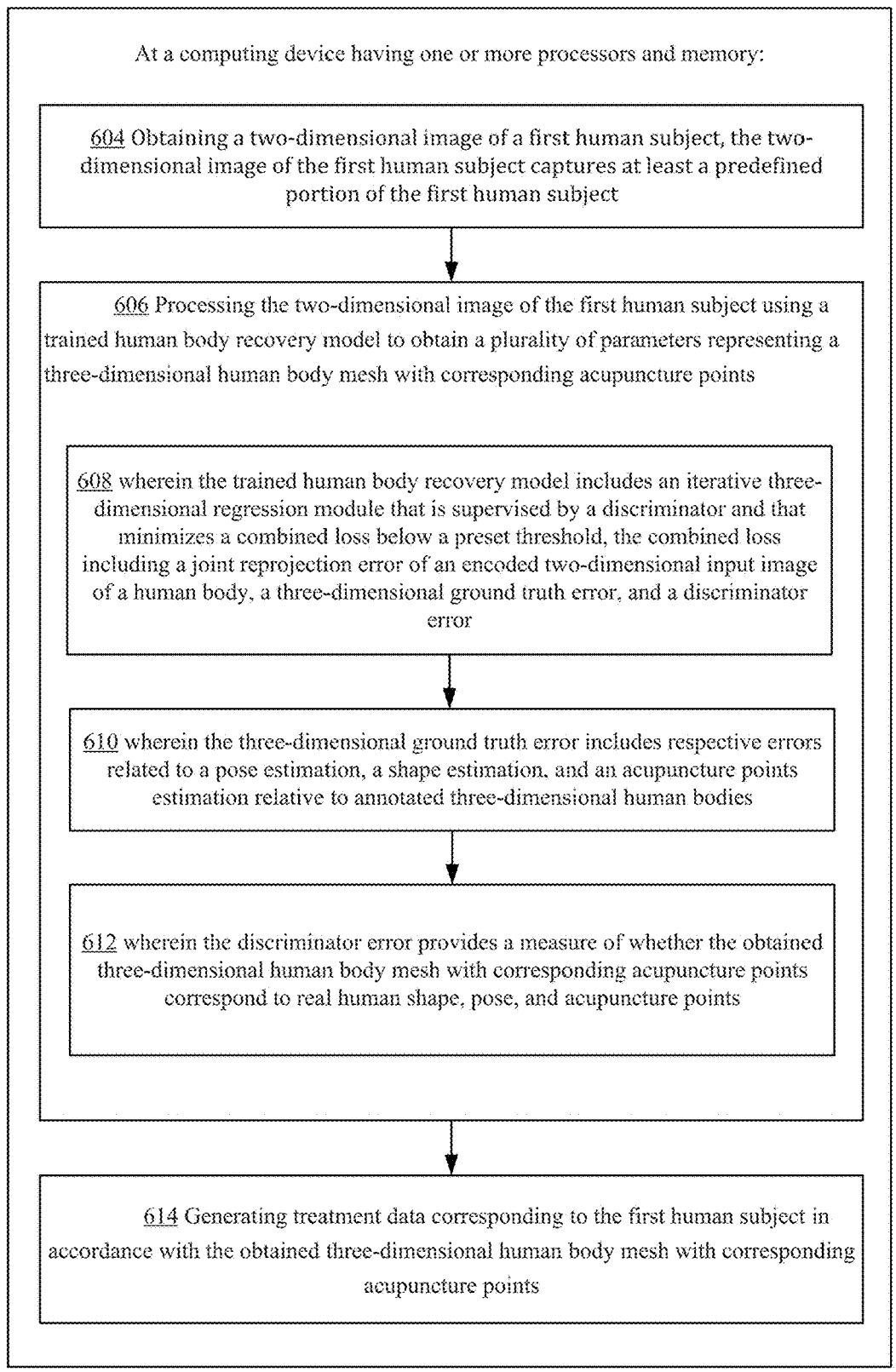
FIG. 6 is a flowchart of a method of generating acupuncture points on reconstructed 3D human body mesh for physical treatment, in accordance with some embodiments.

FIG. 6 is a flowchart of a method 600 of generating acupuncture points on reconstructed 3D human body mesh for physical treatment, in accordance with some embodiments. The method 600 is performed at a computing device (e.g., a central control server 136, a local computing device 114, or a remote computing device 115, FIGS. 1A-1B) having one or more processors and memory. In some embodiments, the computing device is communicably coupled to a therapeutic robot (e.g., robot 128 collocated with the patient 104), and to a guidance device (e.g., computer collocated with the remote expert 110) including a first display generation component and a first input device (e.g., a haptic enabled input device, a touch screen, or a mouse), and wherein the therapeutic robot is collocated with a treatment subject (e.g., a patient 104) and the guidance device is collocated with a treatment guidance provider (e.g., a remote expert 110) during a physical treatment session.

In the method 600, the computing device obtains (604) a first two-dimensional image of a human subject (e.g., the 2D image of the patient 107, FIG. 1A), the first two-dimensional image of the first human subject captures at least a pre-defined portion of the human subject. In some embodiments, the 2D image includes a full body of the patient 104. In some other embodiments, the 2D image includes at least a portion of the patient 104, such as an upper body of the human subject, a lower body of the human subject, or a significant portion of the human body for which pose/posture change is sufficiently discernable in the images, or which includes important acupuncture points for the current physical treatment, such as an arm of the patient, a leg of the patient, the torso of the patient, the head of the patient, an ear of the patient, etc.

In some embodiments, the computing device processes (606) the first two-dimensional image of the first human subject using a trained human body recovery model (e.g., as discussed with reference to FIG. 3) to obtain a plurality of parameters representing a three-dimensional human body mesh (e.g., the 3D human body mesh 197, FIG. 1B) with corresponding acupuncture points (e.g., acupuncture points 118, FIG. 1B). In some embodiments, the trained human body recovery model includes (608) an iterative three-dimensional regression module that is supervised by a discriminator and that minimizes a combined loss (e.g., the combined loss $L=\lambda(L_{reproj}+L_{3D})+L_{adv}$, FIG. 3) below a preset threshold. In some embodiments, the combined loss including a reprojection error (e.g., $L_{reproj}$) of an encoded two-dimensional input image of a human body, a three-dimensional ground truth error (e.g., $L_{3D}$), and a discriminator error (e.g., $L_{adv}$), as discussed with reference to FIG. 3. In some embodiments, the three-dimensional ground truth error includes (610) respective errors related to a pose estimation, a shape estimation, and an acupuncture points estimation relative to annotated three-dimensional human bodies. In some embodiments, the discriminator error provides (612) a measure of whether the obtained three-dimensional human body mesh with corresponding acupuncture points correspond to real human shape, pose, and acupuncture points. In some embodiments, the computing device generates (614) treatment data corresponding to the first human subject in accordance with the obtained three-dimensional human body mesh with corresponding acupuncture points.

In some embodiments, the computing device further trains the human body recovery model using annotated 2D images, annotated 3D human body meshes, and 3D datasets including annotated acupuncture points marked on respective 3D human body meshes. In some embodiments, the 3D datasets are retrieved from acupuncture points database or annotated by TCM doctors on respective 3D human body models.

In some embodiments, the human body recovery model comprises a plurality of human body recovery sub-models corresponding to a plurality of portions of a human body respectively. In some embodiments, the computing device further trains a respective human body recovery sub-model using annotation data of the corresponding portion on the three-dimensional human body corresponding to pose, shape, and a subset of acupuncture points associated with the corresponding portion. In some embodiments, the computing device further reconstructs a portion of a human body with corresponding acupuncture points comprising: dividing a reconstructed 3D full human body mesh into a plurality of reconstructed portions, and identifying a reconstructed portion corresponding to the received 2D image of the portion of the human subject.

In some embodiments, the first two-dimensional image of the first human subject captures a first portion of the first human subject, and wherein the two-dimensional image of the first human subject is processed using a first human body recovery sub-model corresponding to the first portion of the first human subject.

In some embodiments, the computing device further obtains a second two-dimensional image that captures a second portion of the of the human subject that is distinct from the first portion. In some embodiments, the second 2D image is captured in response to a patient movement, TCM doctor's request/change of treatment plan, camera movement, etc. In response, the computing device processes the second two-dimensional image of the second portion of the first human subject using a second human body recovery sub-model to obtain a second set of parameters representing a second three-dimensional human body mesh corresponding to the second portion of the human subject with a second set of acupuncture points associated with the second portion of the first human body. The computing device further updates the treatment data in accordance with the second three-dimensional human body mesh corresponding to the second portion with corresponding second set of acupuncture points.

In some embodiments, the computing device receives a three-dimensional human body database that stores key physical point data corresponding to a plurality of key physical points marked on a respective three-dimensional human body template of a plurality of three-dimensional human body templates, wherein the plurality of key physical points are marked on the respective three-dimensional full-body model based on the received three-dimensional human body database.

In some embodiments, the three dimensional human body database collects data using three-dimensional scanners to obtain the key physical point data of a plurality of key physical points on the respective three-dimensional full-body template. In some embodiments, the three dimensional human body database collects the key physical point data corresponding the a plurality of key physical points that are marked by Traditional Chinese Medicine (TCM) experts on the respective three dimensional human body template.

In some embodiments, the computing device further marks the plurality of key physical points distributed on the respective three-dimensional full-body model by: identifying a plurality of key feature points (e.g., kneecap, shinbone) on the respective three-dimensional full-body model; and identifying a plurality of acupuncture points associated with the respective key feature points. For example, the Three Mile Foot (St 36) acupuncture point is four finger widths below the lower edge of the kneecap and one finger width to the outside of the shinbone. In some embodiments, the TCM experts further adjusts the positions of the acupuncture points based on individual patient's physical characteristics, e.g., finger width varies among different patients, resulting in slightly different acupuncture points locations on different patients.

In some embodiments, prior to processing the first two-dimensional image, the computing device further filters the two-dimensional image, such as removing images that are too obscure, or containing less than a predetermined number of acupuncture points. In some embodiments, the computing device further provides the obtained three-dimensional human body mesh marked with acupuncture points for display on a second computing device (e.g., the display generation component 103) remotely located from the first computing device. The computing device further receives a user input to modify the treatment data associated with one or more acupuncture points on the three-dimensional human body mesh.

It should be understood that the particular order in which the operations in method 600 have been described is merely an example and is not intended to indicate that the described order is the only order in which the operations could be performed. One of ordinary skill in the art would recognize various ways to reorder the operations described herein. Additionally, it should be noted that details of other processes described herein with respect to other methods described herein are also applicable in an analogous manner to method 600 described above with respect to FIG. 6. For brevity, these details are not repeated here.

The operations in the information processing methods described above are, optionally implemented by running one or more functional modules in information processing apparatus such as general purpose processors or application specific chips.

Figure 7:
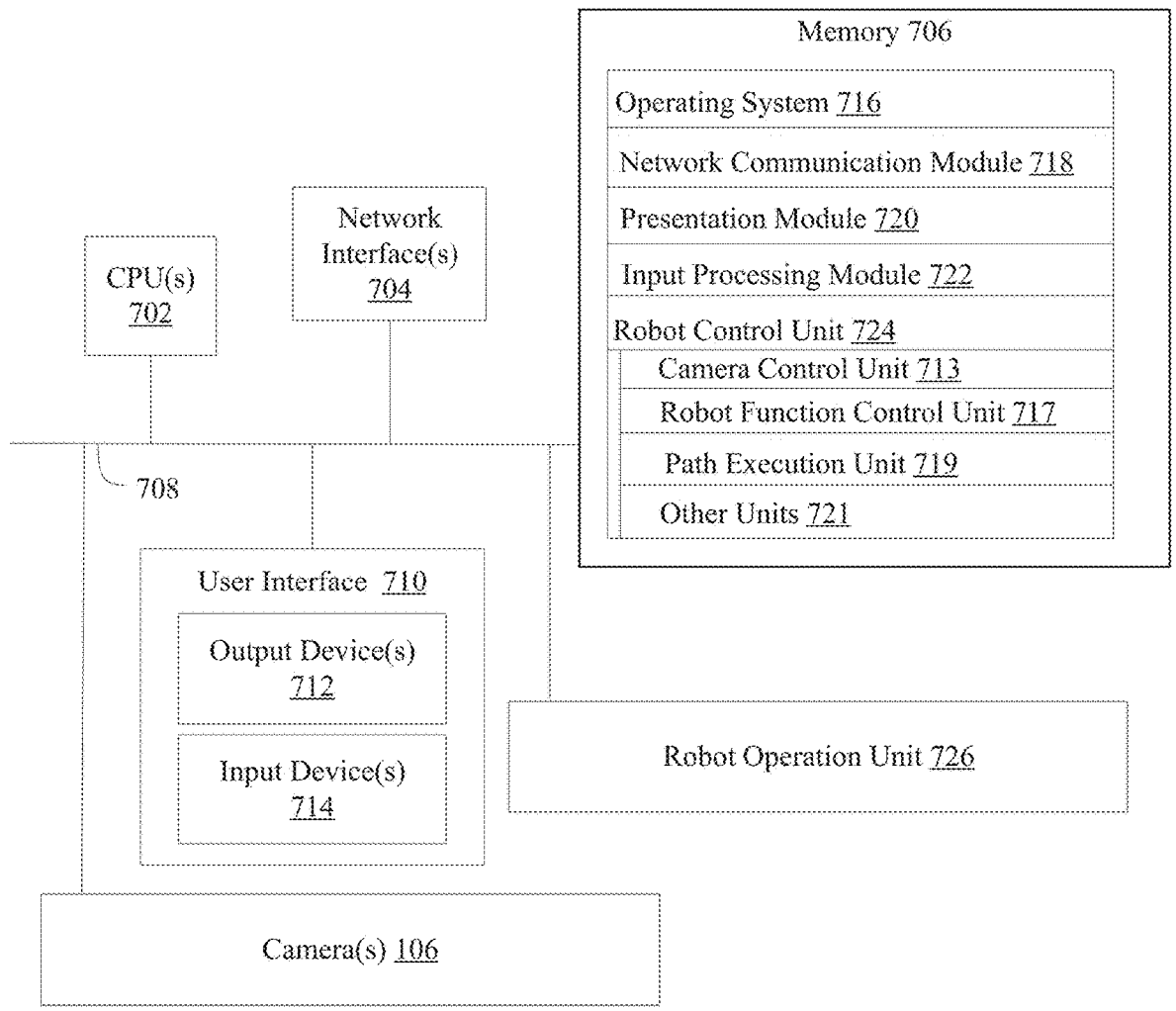
FIG. 7 is a block diagram illustrating an exemplary local site equipment (e.g., a robot) in accordance with some embodiments.

FIG. 7 is a block diagram illustrating local site equipment 700 including an exemplary robot 128 and local-site computing device 114 in accordance with some embodiments.

The local site equipment 700 includes one or more processing units (CPUs) 702, one or more network interfaces 704 (e.g., including the I/O interface to server 136), memory 706, and one or more communication buses 708 for interconnecting these components (sometimes called a chipset). The memory 706 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 706, optionally, includes one or more storage devices remotely located from the one or more processing units 702. The memory 706, or alternatively the non-volatile memory within the memory 706, includes a non-transitory computer readable storage medium. In some implementations, the memory 706, or the non-transitory computer readable storage medium of the memory 706, stores the following programs, modules, and data structures, or a subset or superset thereof:

Operating system 716 including procedures for handling various basic system services and for performing hardware dependent tasks;

Network communication module 718 for connecting the robot 128 to other computing devices;

Presentation module 720 for enabling presentation of information at the robot 128 via the one or more output devices 712 (e.g., displays, speakers, etc.) associated with the user interface 710;

Input processing module 722 for detecting one or more user inputs or interactions from one of the one or more input devices 714 and interpreting the detected input or interaction;

Control Unit 724 for controlling functions of the robot 128 and the local site equipment, including camera control unit 713 for controlling camera(s) 106 of the robot 128, robot function control unit 717 for controlling the robot operation unit 726 of the robot, path execution unit 719 for executing a path in accordance with a high level instructions of a path planner, and other units for implementing the functions of the robot 128 as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 706, optionally, stores a subset of the modules and data structures identified above. Furthermore, the memory 706, optionally, stores additional modules and data structures not described above.

In some implementations, at least some of the functions of the local-site equipment are performed by the server 136, and the corresponding sub-modules of these functions may be located within the server 136 rather than the local-site equipment. The local-site equipment shown in FIG. 7 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 706, optionally, stores a subset of the modules and data structures identified above. Furthermore, the memory 706, optionally, stores additional modules and data structures not described above.

Figure 8:
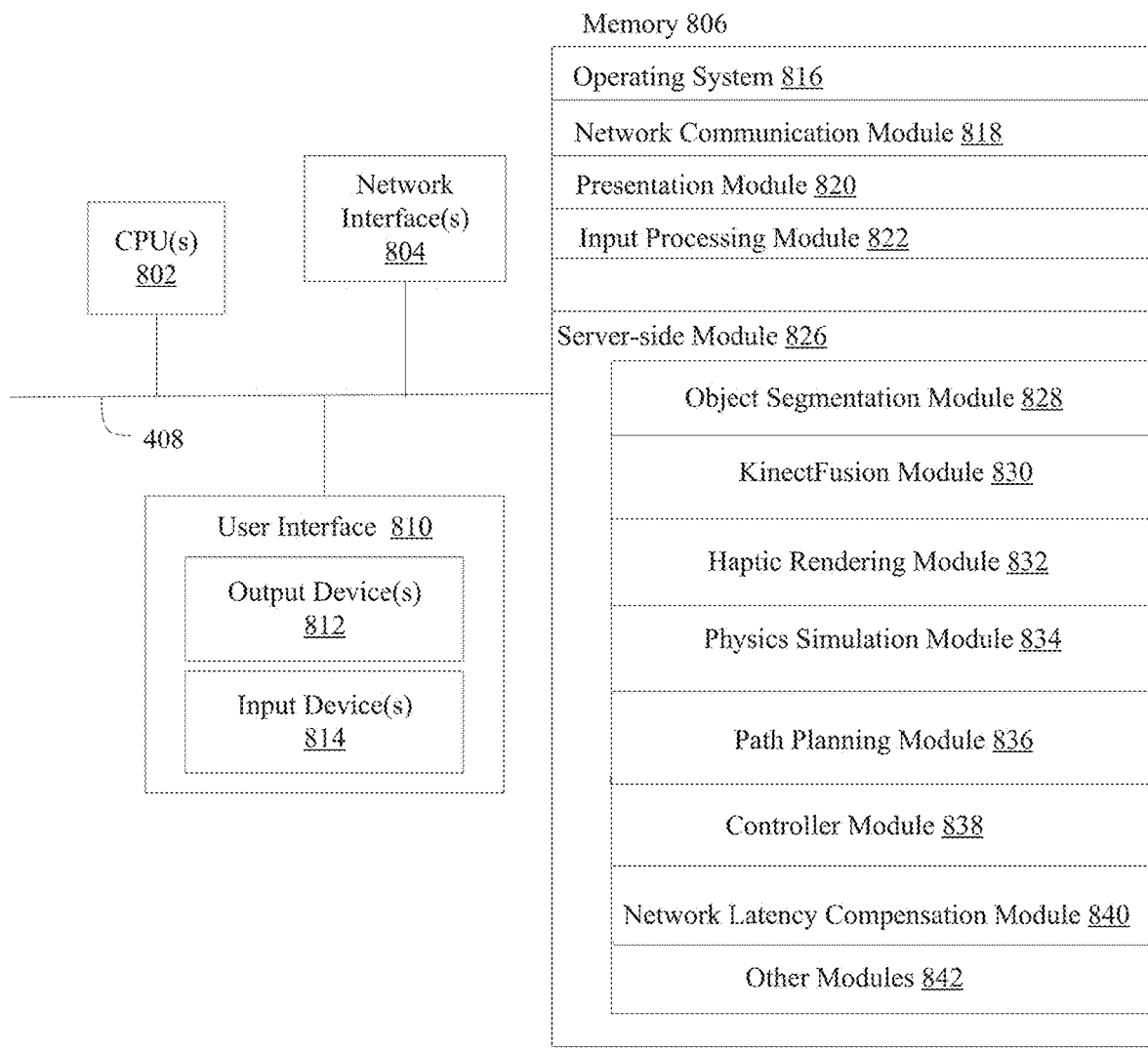
FIG. 8 is a block diagram illustrating an exemplary server in accordance with some implementations.

FIG. 8 is a block diagram illustrating an exemplary server 136 in accordance with some implementations. The server system 136, typically, includes one or more processing units (CPUs) 802, one or more network interfaces 804 (e.g., including the I/O interface to one or more robots 128 and the I/O interface to one or more user-side devices, such as local site equipment 700 and remote site equipment 900), memory 806, and one or more communication buses 808 for interconnecting these components (sometimes called a chipset). The memory 806 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 806, optionally, includes one or more storage devices remotely located from the one or more processing units 802. The memory 806, or alternatively the non-volatile memory within the memory 806, includes a non-transitory computer readable storage medium. In some implementations, the memory 806, or the non-transitory computer readable storage medium of the memory 806, stores the following programs, modules, and data structures, or a subset or superset thereof:

Operating system 816 including procedures for handling various basic system services and for performing hardware dependent tasks;

Network communication module 818 for connecting the server 136 to other computing devices (e.g., the local site equipment 700 (e.g., cameras and sensors, and computing devices) and the remote site equipment 900 (e.g., including input devices (e.g., device 111), display devices, and computing devices));

Presentation module 820 for enabling presentation of information at the server 136 via the one or more output devices 812 (e.g., displays, speakers, etc.) associated with the user interface 810;

Input processing module 822 for detecting one or more user inputs or interactions from one of the one or more input devices 814 and interpreting the detected input or interaction;

Server-side modules 826 for controlling functions of the server 136, including object segmentation module 828 for performing object segmentation in the virtualized environment, KinectFusion module 830 for generating and updating the virtualized environment based on the image data stream received from the robot, Haptic rendering module 832 for generating haptic feedback based on the user's input provided via the haptic enabled input device and based on the location of the input in the virtualized environment, physics simulation module for generating reaction and friction force rendering as well as object interaction models in the virtualized environment, path planning module 836 for generating a planned path based on the virtualized environment and haptics markings and virtual objects present in the virtualized environment, controller module 838 for controlling path execution by the robot, network latency compensation module 840 for adjusting path planning based on network delays, and other modules 842 for implementing other functions (e.g., modules 138, 140, 142, 144, 146, 144, 146, 150, 152, 154, 156, and 158) of the server 136 as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 806, optionally, stores a subset of the modules and data structures identified above. Furthermore, the memory 806, optionally, stores additional modules and data structures not described above.

In some implementations, at least some of the functions of the server 136 are performed by the robot 128, the local-site computing device 114, or the remote-site computing device 115, and the corresponding sub-modules of these functions may be located within the robot, the local-site computing device 114, or the remote-site computing device 115, rather than the server 136. The server 136 shown in FIG. 8 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 806, optionally, stores a subset of the modules and data structures identified above. Furthermore, the memory 806, optionally, stores additional modules and data structures not described above.

Figure 9:
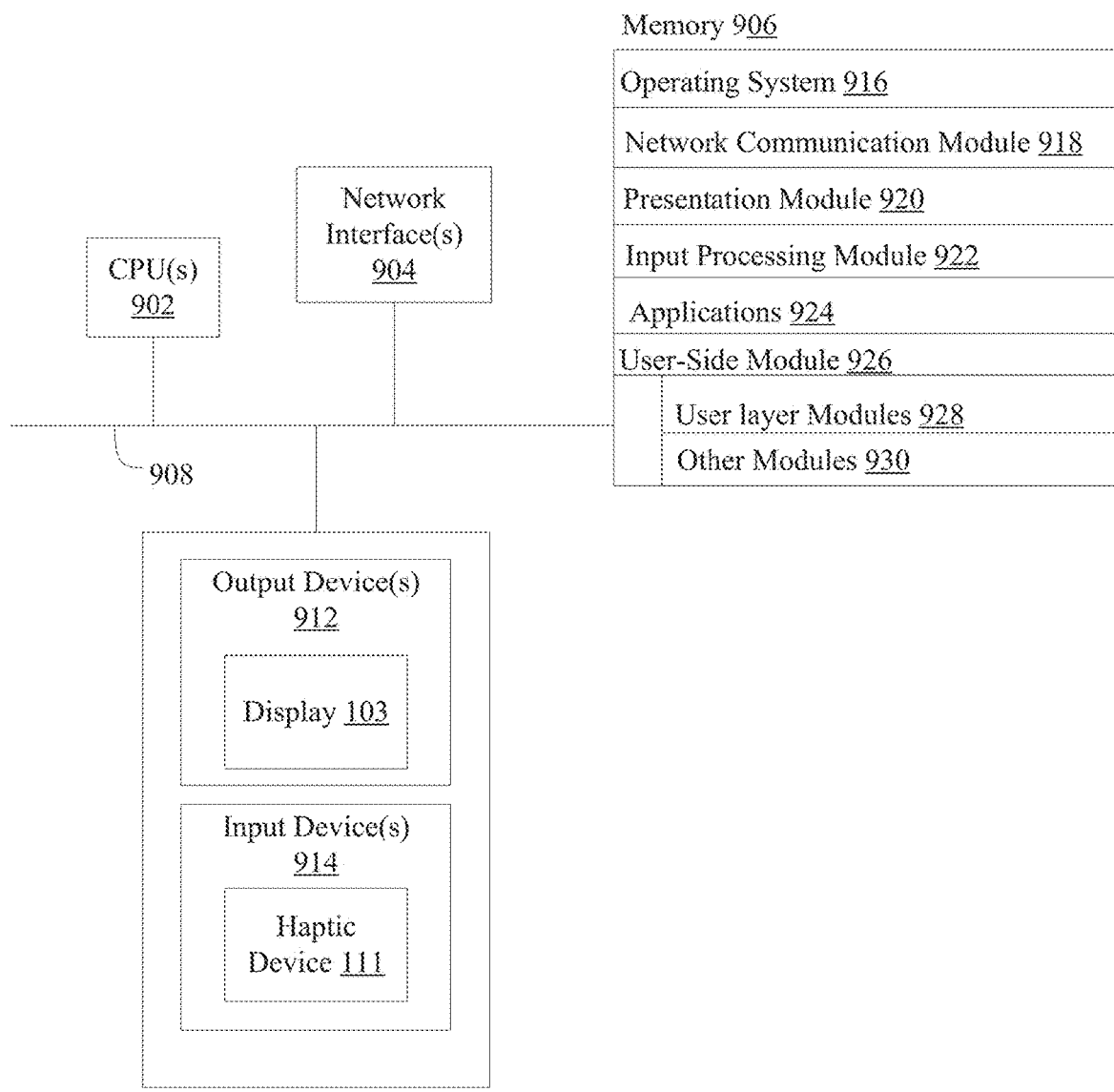
FIG. 9 is a block diagram illustrating an exemplary expert-side device in accordance with some implementations.

FIG. 9 is a block diagram illustrating an exemplary remote-site device 900 in accordance with some implementations. The remote site device 900, typically, includes one or more processing units (CPUs) 902, one or more network interfaces 904 (e.g., including the I/O interface to server 110), memory 906, and one or more communication buses 908 for interconnecting these components (sometimes called a chipset). The memory 906 includes high-speed random access memory, such as DRAM, SRAM, DDR RAM, or other random access solid state memory devices; and, optionally, includes non-volatile memory, such as one or more magnetic disk storage devices, one or more optical disk storage devices, one or more flash memory devices, or one or more other non-volatile solid state storage devices. The memory 906, optionally, includes one or more storage devices remotely located from the one or more processing units 902. The memory 906, or alternatively the non-volatile memory within the memory 906, includes a non-transitory computer readable storage medium. In some implementations, the memory 906, or the non-transitory computer readable storage medium of the memory 906, stores the following programs, modules, and data structures, or a subset or superset thereof:

- Operating system 916 including procedures for handling various basic system services and for performing hardware dependent tasks;
- Network communication module 918 for connecting the server 136 to other computing devices;
- Presentation module 920 for enabling presentation of information at the remote-side device 900 via the one or more output devices 912 (e.g., displays 103, speakers, haptic-enabled input device 111, etc.) associated with the user interface 910;
- Input processing module 922 for detecting one or more user inputs or interactions from one of the one or more input devices 914 (e.g., haptic-enabled input device 111) and interpreting the detected input or interaction;
- Applications 924 for implementing various user-level functions, such as word processing, drawing, etc.
- User-side modules 926 for controlling functions of the user-side devices, including user layer module 928 and other modules 930 for implementing other functions of the user-side device as described herein.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, modules or data structures, and thus various subsets of these modules may be combined or otherwise re-arranged in various implementations. In some implementations, memory 906, optionally, stores a subset of the modules and data structures identified above. Furthermore, the memory 906, optionally, stores additional modules and data structures not described above.

In some implementations, at least some of the functions of the server 136 are performed by the remote-site device 900, and the corresponding sub-modules of these functions may be located within the server rather than the remote-site device 900. The remote-site device 900 shown in FIG. 9 is merely illustrative, and different configurations of the modules for implementing the functions described herein are possible in various implementations.

Each of the above identified elements may be stored in one or more of the previously mentioned memory devices, and corresponds to a set of instructions for performing a function described above. The above identified modules or programs (i.e., sets of instructions) need not be implemented as separate software programs, procedures, or modules, and thus various subsets of these modules may be combined or otherwise re-arranged in various implementations. In some implementations, the memory 906, optionally, stores a subset of the modules and data structures identified above. Furthermore, the memory 906, optionally, stores additional modules and data structures not described above.

What is claimed is:

1. A method, comprising:
   at a computing system having one or more processors and memory:
      obtaining a first two-dimensional image of a human subject, the first two-dimensional image of the first human subject captures at least a predefined portion of the human subject;
      processing the first two-dimensional image of the first human subject using a trained human body recovery model to obtain a plurality of parameters representing a three-dimensional human body mesh with corresponding acupuncture points, wherein:
         the trained human body recovery model includes an iterative three-dimensional regression module that is supervised by a discriminator and that minimizes a combined loss below a preset threshold, the combined loss including a reprojection error of an encoded two-dimensional input image of a human body, a three-dimensional ground truth error, and a discriminator error,
         the three-dimensional ground truth error includes respective errors related to a pose estimation, a shape estimation, and an acupuncture points estimation relative to annotated three-dimensional human bodies, and
         the discriminator error provides a measure of whether the obtained three-dimensional human body mesh with corresponding acupuncture points corresponds to real human shape, pose, and acupuncture points; and
      generating treatment data corresponding to the first human subject in accordance with the obtained three-dimensional human body mesh with corresponding acupuncture points.

2. The method of claim 1, further comprising training the human body recovery model using annotated 2D images, annotated 3D human body meshes, and 3D datasets including annotated acupuncture points marked on respective 3D human body meshes.

3. The method of claim 1, wherein the human body recovery model comprises a plurality of human body recovery sub-models corresponding to a plurality of portions of a human body respectively.

4. The method of claim 3, further comprising training a respective human body recovery sub-model using annotation data of the corresponding portion on the three-dimensional human body corresponding to pose, shape, and a subset of acupuncture points associated with the corresponding portion.

5. The method of claim 3, further comprising reconstructing a portion of a human body with corresponding acupuncture points, comprising:
   dividing a reconstructed 3D full human body mesh into a plurality of reconstructed portions; and
   identifying a reconstructed portion corresponding to the received 2D image of the portion of the human subject.

6. The method of claim 1, wherein the first two-dimensional image of the first human subject captures a first portion of the first human subject, and wherein the two-dimensional image of the first human subject is processed using a first human body recovery sub-model corresponding to the first portion of the first human subject.

7. The method of claim 1, further comprising:
   obtaining a second two-dimensional image that captures a second portion of the of the human subject that is distinct from the first portion;
   processing the second two-dimensional image of the second portion of the first human subject using a second human body recovery sub-model to obtain a second set of parameters representing a second three-dimensional human body mesh corresponding to the second portion of the human subject with a second set of acupuncture points associated with the second portion of the first human body; and
   updating the treatment data in accordance with the second three-dimensional human body mesh corresponding to the second portion with a corresponding second set of acupuncture points.

8. A computing device, comprising:
   one or more processors; and
   memory storing instructions, wherein the instructions, when executed by the one or more processors, cause the processors to perform operations comprising:
      obtaining a first two-dimensional image of a human subject, the first two-dimensional image of the first human subject captures at least a predefined portion of the human subject;
      processing the first two-dimensional image of the first human subject using a trained human body recovery model to obtain a plurality of parameters representing a three-dimensional human body mesh with corresponding acupuncture points, wherein:
         the trained human body recovery model includes an iterative three-dimensional regression module that is supervised by a discriminator and that minimizes a combined loss below a preset threshold, the combined loss including a reprojection error of an encoded two-dimensional input image of a human body, a three-dimensional ground truth error, and a discriminator error,
         the three-dimensional ground truth error includes respective errors related to a pose estimation, a shape estimation, and an acupuncture points estimation relative to annotated three-dimensional human bodies, and
         the discriminator error provides a measure of whether the obtained three-dimensional human body mesh with corresponding acupuncture points corresponds to real human shape, pose, and acupuncture points; and
      generating treatment data corresponding to the first human subject in accordance with the obtained three-dimensional human body mesh with corresponding acupuncture points.

9. The computing device of claim 8, wherein the operations include training the human body recovery model using annotated 2D images, annotated 3D human body meshes, and 3D datasets including annotated acupuncture points marked on respective 3D human body meshes.

10. The computing device of claim 8, wherein the human body recovery model comprises a plurality of human body recovery sub-models corresponding to a plurality of portions of a human body respectively.

11. The computing device of claim 10, wherein the operations include training a respective human body recovery sub-model using annotation data of the corresponding portion on the three-dimensional human body corresponding to pose, shape, and a subset of acupuncture points associated with the corresponding portion.

12. The computing device of claim 10, wherein the operations further include reconstructing a portion of a human body with corresponding acupuncture points, comprising:
   dividing a reconstructed 3D full human body mesh into a plurality of reconstructed portions; and
   identifying a reconstructed portion corresponding to the received 2D image of the portion of the human subject.

13. The computing device of claim 8, wherein the first two-dimensional image of the first human subject captures a first portion of the first human subject, and wherein the two-dimensional image of the first human subject is processed using a first human body recovery sub-model corresponding to the first portion of the first human subject.

14. The computing device of claim 8, wherein the operations further include:
   obtaining a second two-dimensional image that captures a second portion of the human subject that is distinct from the first portion;
   processing the second two-dimensional image of the second portion of the first human subject using a second human body recovery sub-model to obtain a second set of parameters representing a second three-dimensional human body mesh corresponding to the second portion of the human subject with a second set of acupuncture points associated with the second portion of the first human body; and
   updating the treatment data in accordance with the second three-dimensional human body mesh corresponding to the second portion with a corresponding second set of acupuncture points.

15. A non-transitory computer-readable storage medium stores instructions, the instructions, when executed by one or more processors of a computing device, cause the computing device to perform operations comprising:
   obtaining a first two-dimensional image of a human subject, the first two-dimensional image of the first human subject captures at least a predefined portion of the human subject;
   processing the first two-dimensional image of the first human subject using a trained human body recovery model to obtain a plurality of parameters representing a three-dimensional human body mesh with corresponding acupuncture points, wherein:
the trained human body recovery model includes an iterative three-dimensional regression module that is supervised by a discriminator and that minimizes a combined loss below a preset threshold, the combined loss including a reprojection error of an encoded two-dimensional input image of a human body, a three-dimensional ground truth error, and a discriminator error,
the three-dimensional ground truth error includes respective errors related to a pose estimation, a shape estimation, and an acupuncture points estimation relative to annotated three-dimensional human bodies, and
the discriminator error provides a measure of whether the obtained three-dimensional human body mesh with corresponding acupuncture points corresponds to real human shape, pose, and acupuncture points; and
generating treatment data corresponding to the first human subject in accordance with the obtained three-dimensional human body mesh with corresponding acupuncture points.

16. The non-transitory computer-readable storage medium of claim 15, wherein the operations include training the human body recovery model using annotated 2D images, annotated 3D human body meshes, and 3D datasets including annotated acupuncture points marked on respective 3D human body meshes.

17. The non-transitory computer-readable storage medium of claim 15, wherein the human body recovery model comprises a plurality of human body recovery sub-models corresponding to a plurality of portions of a human body respectively.

18. The non-transitory computer-readable storage medium of claim 17, wherein the operations further comprise reconstructing a portion of a human body with corresponding acupuncture points, comprising:
dividing a reconstructed 3D full human body mesh into a plurality of reconstructed portions; and
identifying a reconstructed portion corresponding to the received 2D image of the portion of the human subject.

19. The non-transitory computer-readable storage medium of claim 15, wherein the first two-dimensional image of the first human subject captures a first portion of the first human subject, and wherein the two-dimensional image of the first human subject is processed using a first human body recovery sub-model corresponding to the first portion of the first human subject.

20. The non-transitory computer-readable storage medium of claim 15, wherein the operations include:
obtaining a second two-dimensional image that captures a second portion of the human subject that is distinct from the first portion;
processing the second two-dimensional image of the second portion of the first human subject using a second human body recovery sub-model to obtain a second set of parameters representing a second three-dimensional human body mesh corresponding to the second portion of the human subject with a second set of acupuncture points associated with the second portion of the first human body; and
updating the treatment data in accordance with the second three-dimensional human body mesh corresponding to the second portion with a corresponding second set of acupuncture points.

* * * * *